US010766666B2

(12) United States Patent
 Cirou et al.

(10) Patent No.: US 10,766,666 B2
(45) Date of Patent: *Sep. 8, 2020

(54) DEVICE FOR A BIOLOGICAL LIQUID TREATMENT INSTALLATION

(71) Applicant: EMD Millipore Corporation, Burlington, MA (US)

(72) Inventors: Sebastien Cirou, Schiltigheim (FR); Rene Reinbigler, Kirchheim (FR); Virginie Buisson, Wolfisheim (FR); Jean-Louis Weissenbach, Ville (FR)

(73) Assignee: EMD Millipore Corporation, Burlington, MA (US)

( * ) Notice: Subject to any disclaimer, the term of this patent is extended or adjusted under 35 U.S.C. 154(b) by 371 days.

This patent is subject to a terminal disclaimer.

(21) Appl. No.: 15/848,156

(22) Filed: Dec. 20, 2017

(65) Prior Publication Data

US 2018/0111720 A1   Apr. 26, 2018

Related U.S. Application Data

(60) Continuation of application No. 13/872,248, filed on Apr. 29, 2013, now abandoned, which is a division of
(Continued)

(30) Foreign Application Priority Data

Jun. 8, 2010 (FR) ..................................... 10 54517

(51) Int. Cl.
 *B65D 33/00* (2006.01)
 *A61M 1/36* (2006.01)
(Continued)

(52) U.S. Cl.
 CPC .............. *B65D 33/00* (2013.01); *A61M 1/36* (2013.01); *B01D 61/18* (2013.01); *B01D 61/20* (2013.01);
(Continued)

(58) Field of Classification Search
 CPC ... B65B 33/00; A61M 1/36; A61M 2205/125; A61M 2209/088; A61M 2209/082; A61M 2209/084
 See application file for complete search history.

(56) References Cited

U.S. PATENT DOCUMENTS 2,413,853 A    1/1947  Zademach et al.
2,787,403 A    4/1957  Carr et al.
(Continued)

FOREIGN PATENT DOCUMENTS

CN      101281204 A     10/2008
DE      102006059459 A1  7/2008
(Continued)

OTHER PUBLICATIONS

Notice of allowance dated Oct. 1, 2018 in co-pending U.S. Appl. No. 15/161,768.
(Continued)

*Primary Examiner* — Katherine Zalasky McDonald
(74) *Attorney, Agent, or Firm* — Nields, Lemack & Frame, LLC

(57) ABSTRACT

The invention concerns a device comprising a base (2) and a door (20), said device having a closed door position in which a circuit (8) of the device comprises a bag comprising two flexible films and connectors of the conveying network, and a press (9) comprising a first shell (16) disposed on a front face (5) of said base (2) and a second shell (17) disposed in said door (20); and a hinge system hinging said door (20) relative to said base (2), and disposed only on one side of said door (20) so as to form lateral clearances between said door (20) and said base (2) over the rest of a perimeter of said door (20).

8 Claims, 14 Drawing Sheets

Related U.S. Application Data application No. 13/153,804, filed on Jun. 6, 2011, now Pat. No. 9,205,955.

(51) Int. Cl.
  *B01D 61/18* (2006.01)
  *B01D 61/20* (2006.01)
  *F04B 43/08* (2006.01)

(52) U.S. Cl.
  CPC ....... *F04B 43/08* (2013.01); *A61M 2205/125* (2013.01); *A61M 2209/088* (2013.01); *B01D 2313/105* (2013.01); *B01D 2313/125* (2013.01); *B01D 2313/58* (2013.01)

(56) References Cited

U.S. PATENT DOCUMENTS

| | | |
|---|---|---|
| 2,941,575 A | 6/1960 | Malmberg et al. |
| 2,943,738 A | 7/1960 | Schmidt, Jr. |
| 3,022,229 A | 2/1962 | Heden |
| 3,179,117 A | 4/1965 | Gibson et al. |
| 3,527,572 A | 9/1970 | Urkiewicz |
| 3,596,554 A | 8/1971 | Low et al. |
| 3,667,487 A | 6/1972 | Schoenbeck et al. |
| 3,772,154 A | 11/1973 | Isenberg et al. |
| 3,774,762 A | 11/1973 | Lichtenstein |
| 3,845,765 A | 11/1974 | Ikeda |
| 4,113,623 A | 11/1978 | Koether et al. |
| 4,198,972 A | 4/1980 | Herb |
| 4,285,464 A | 8/1981 | Latham |
| 4,332,750 A | 6/1982 | Roggenburg et al. |
| 4,370,983 A | 2/1983 | Lichtenstein |
| 4,466,888 A | 8/1984 | Verkaart |
| 4,610,781 A | 9/1986 | Bilstad et al. |
| 4,775,360 A | 10/1988 | Lane et al. |
| 4,784,751 A | 11/1988 | McGehee |
| 4,790,118 A | 12/1988 | Chilcoate |
| 4,852,851 A | 8/1989 | Webster |
| 4,855,236 A | 8/1989 | Levin |
| 4,915,119 A | 4/1990 | Franklin |
| 5,019,257 A | 5/1991 | Suzuki et al. |
| 5,061,236 A | 10/1991 | Sutherland et al. |
| 5,141,866 A | 8/1992 | Levin |
| 5,265,912 A | 11/1993 | Natividad |
| 5,290,518 A | 3/1994 | Johnson |
| 5,306,420 A | 4/1994 | Bisconte |
| 5,324,422 A | 6/1994 | Colleran et al. |
| 5,342,463 A | 8/1994 | Addeo et al. |
| 5,427,509 A | 6/1995 | Chapman et al. |
| 5,462,416 A | 10/1995 | Dennehey et al. |
| 5,520,885 A | 5/1996 | Coelho et al. |
| 5,628,908 A | 5/1997 | Kamen et al. |
| 5,645,723 A | 7/1997 | Fujishiro et al. |
| 5,678,568 A | 10/1997 | Uchikubo et al. |
| 5,711,916 A | 1/1998 | Riggs et al. |
| 5,738,645 A | 4/1998 | Plotkin |
| 5,985,653 A | 11/1999 | Armstrong et al. |
| 6,073,942 A | 6/2000 | Heneveld |
| 6,099,734 A | 8/2000 | Boggs |
| 6,129,099 A | 10/2000 | Foster et al. |
| 6,146,124 A | 11/2000 | Coelho et al. |
| 6,186,998 B1 | 2/2001 | Inuzuka et al. |
| 6,213,334 B1 | 4/2001 | Coelho et al. |
| 6,228,255 B1 | 5/2001 | Peterson et al. |
| 6,232,115 B1 | 5/2001 | Coelho et al. |
| 6,303,025 B1 | 10/2001 | Houchens |
| 6,361,642 B1 | 3/2002 | Bellamy et al. |
| 6,386,789 B1 | 5/2002 | Chausse et al. |
| 6,670,169 B1 | 12/2003 | Schoeb et al. |
| 6,764,761 B2 | 7/2004 | Eu et al. |
| 6,808,675 B1 | 10/2004 | Coelho et al. |
| 6,818,185 B1 | 11/2004 | Petersen et al. |
| 6,868,987 B2 | 3/2005 | Hedington et al. |
| 6,902,706 B1 | 6/2005 | Colin et al. |
| 6,982,063 B2 | 1/2006 | Hamel et al. |
| 7,115,205 B2 | 10/2006 | Robinson et al. |
| 7,153,286 B2 | 12/2006 | Busby et al. |
| 7,326,355 B2 | 2/2008 | Graetz et al. |
| 7,458,560 B2 | 12/2008 | Muller |
| 7,485,224 B2 | 2/2009 | Jones et al. |
| 7,648,627 B2 | 1/2010 | Beden et al. |
| 7,666,602 B2 | 2/2010 | Ammann et al. |
| 7,867,189 B2 | 1/2011 | Childers et al. |
| 7,935,074 B2 | 5/2011 | Plahey et al. |
| 7,935,253 B2 | 5/2011 | Beulay et al. |
| 8,114,276 B2 | 2/2012 | Childers et al. |
| 8,163,172 B2 | 4/2012 | Beulay et al. |
| 8,343,356 B2 | 1/2013 | Beulay et al. |
| 8,383,397 B2 | 2/2013 | Wojciechowski et al. |
| 8,499,794 B2 | 8/2013 | Takahashi et al. |
| 8,505,959 B2 | 8/2013 | Darling |
| 8,506,798 B2 | 8/2013 | Beulay et al. |
| 8,557,113 B2 | 10/2013 | Beulay et al. |
| 8,900,454 B2 | 12/2014 | Cirou et al. |
| 8,906,229 B2 | 12/2014 | Cirou et al. |
| 8,916,045 B2 | 12/2014 | Reinbigler et al. |
| 8,921,096 B2 | 12/2014 | Weissenbach et al. |
| 9,051,929 B2 | 6/2015 | Cirou et al. |
| 9,171,145 B2 | 10/2015 | Dash et al. |
| 9,174,145 B2 | 11/2015 | Weissenbach et al. |
| 9,174,171 B2 | 11/2015 | Weissenbach et al. |
| 9,181,941 B2 | 11/2015 | Cirou et al. |
| 9,205,955 B2 | 12/2015 | Cirou et al. |
| 9,259,687 B2 | 2/2016 | Weissenbach et al. |
| 9,259,733 B2 | 2/2016 | Tuccelli et al. |
| 9,523,072 B2 | 12/2016 | Reinbigler et al. |
| 9,528,085 B2 | 12/2016 | Reinbigler et al. |
| 9,739,424 B2 | 8/2017 | Cirou et al. |
| 9,744,487 B2 | 8/2017 | Cirou et al. |
| 9,777,847 B2 | 10/2017 | Tuccelli et al. |
| 2002/0147423 A1 | 10/2002 | Burbank et al. |
| 2003/0040104 A1 | 2/2003 | Barbera-Guillem |
| 2003/0199803 A1 | 10/2003 | Robinson et al. |
| 2004/0031507 A1 | 2/2004 | Ross et al. |
| 2004/0031756 A1 | 2/2004 | Suzuki et al. |
| 2004/0104153 A1 | 6/2004 | Yang |
| 2004/0222341 A1 | 11/2004 | Breda et al. |
| 2004/0259240 A1 | 12/2004 | Fadden |
| 2005/0254879 A1 | 11/2005 | Gundersen et al. |
| 2006/0024212 A1 | 2/2006 | Hwang |
| 2006/0057030 A1 | 3/2006 | Lee et al. |
| 2006/0118472 A1 | 6/2006 | Schick et al. |
| 2006/0226333 A1 | 10/2006 | Newkirk |
| 2007/0095364 A1 | 5/2007 | Watt |
| 2007/0112297 A1 | 5/2007 | Plahey et al. |
| 2007/0128087 A1 | 6/2007 | Cannizzaro et al. |
| 2007/0199875 A1 | 8/2007 | Moorey et al. |
| 2007/0278155 A1 | 12/2007 | Lo et al. |
| 2008/0023045 A1 | 1/2008 | Miller et al. |
| 2008/0057274 A1 | 3/2008 | Hagiwara et al. |
| 2008/0213143 A1 | 9/2008 | Gyonouchi et al. |
| 2008/0254962 A1 | 10/2008 | Mizuo et al. |
| 2009/0011179 A1 | 1/2009 | Kikuchi et al. |
| 2009/0042293 A1 | 2/2009 | Hata et al. |
| 2009/0050756 A1 | 2/2009 | Newkirk et al. |
| 2009/0101219 A1 | 4/2009 | Martini et al. |
| 2009/0101552 A1 | 4/2009 | Fulkerson et al. |
| 2009/0111179 A1 | 4/2009 | Hata et al. |
| 2009/0180933 A1 | 7/2009 | Kauling et al. |
| 2009/0215602 A1 | 8/2009 | Min et al. |
| 2009/0294349 A1 | 12/2009 | Beulay et al. |
| 2009/0314970 A1 | 12/2009 | McAvoy et al. |
| 2010/0108920 A1 | 5/2010 | Tatarek |
| 2010/0126927 A1 | 5/2010 | Blankenstein et al. |
| 2010/0187167 A1 | 7/2010 | Reinbigler et al. |
| 2010/0204765 A1 | 8/2010 | Hall et al. |
| 2010/0206785 A1 | 8/2010 | Beulay et al. |
| 2010/0234805 A1 | 9/2010 | Kaufmann et al. |
| 2011/0174716 A1 | 7/2011 | Beulay et al. |
| 2011/0297866 A1 | 12/2011 | Weber |
| 2011/0303306 A1 | 12/2011 | Weber |
| 2011/0315611 A1 | 12/2011 | Fulkerson et al. |
| 2012/0006736 A1 | 1/2012 | Cirou et al. |
| 2012/0018018 A1 | 1/2012 | Cirou et al. |

(56) References Cited

U.S. PATENT DOCUMENTS

| | | |
|---|---|---|
| 2012/0031510 A1 | 2/2012 | Weissenbach et al. |
| 2012/0053520 A1 | 3/2012 | Kirkpatrick |
| 2012/0138173 A1 | 6/2012 | Cirou et al. |
| 2012/0138522 A1 | 6/2012 | Cirou et al. |
| 2012/0145616 A1 | 6/2012 | Weissenbach et al. |
| 2012/0160342 A1 | 6/2012 | Weissenbach et al. |
| 2012/0160356 A1 | 6/2012 | Reinbigler et al. |
| 2012/0168390 A1 | 7/2012 | Beulay et al. |
| 2012/0248025 A1 | 10/2012 | Reinbigler et al. |
| 2012/0284991 A1 | 11/2012 | Kusz et al. |
| 2013/0087490 A1 | 4/2013 | Beulay et al. |
| 2013/0193073 A1 | 8/2013 | Hogard et al. |
| 2013/0210130 A1 | 8/2013 | Larcher et al. |
| 2013/0236130 A1 | 9/2013 | Cirou et al. |
| 2013/0240065 A1 | 9/2013 | Weissenbach et al. |
| 2013/0292319 A1 | 11/2013 | Fulkerson et al. |
| 2014/0069537 A1 | 3/2014 | Cirou et al. |
| 2014/0112828 A1 | 4/2014 | Grant et al. |
| 2014/0263062 A1 | 9/2014 | Updyke et al. |
| 2015/0008184 A1 | 1/2015 | Cirou et al. |
| 2015/0013773 A1 | 1/2015 | Cirou et al. |
| 2015/0083320 A1 | 3/2015 | Putnam |
| 2015/0190809 A1 | 7/2015 | Tuccelli et al. |
| 2015/0204450 A1 | 7/2015 | Tuccelli et al. |
| 2016/0264923 A1 | 9/2016 | Reinbigler et al. |

FOREIGN PATENT DOCUMENTS

| | | |
|---|---|---|
| DE | 102008003823 A1 | 7/2008 |
| EP | 0040427 A1 | 11/1981 |
| EP | 0479047 A2 | 4/1992 |
| EP | 0803723 A1 | 10/1997 |
| EP | 1195171 A2 | 4/2002 |
| EP | 1239227 A1 | 9/2002 |
| EP | 2044964 A2 | 4/2009 |
| EP | 2130903 A1 | 12/2009 |
| EP | 2208534 A1 | 7/2010 |
| EP | 2210666 A1 | 7/2010 |
| EP | 2228635 A1 | 9/2010 |
| FR | 2241615 A1 | 3/1975 |
| FR | 2673853 A1 | 9/1992 |
| FR | 2931838 A1 | 12/2009 |
| FR | 2940145 A1 | 6/2010 |
| FR | 2955119 A1 | 7/2011 |
| FR | 2960796 A1 | 12/2011 |
| FR | 2961711 A1 | 12/2011 |
| GB | 1434786 A | 5/1976 |
| GB | 2448858 A | 11/2008 |
| JP | 62-081543 A | 4/1987 |
| JP | 2010-502405 A | 1/2010 |
| WO | 93/03295 A1 | 2/1993 |
| WO | 94/05346 A1 | 3/1994 |
| WO | 00/48703 A1 | 8/2000 |
| WO | 2005/090403 A2 | 9/2005 |
| WO | 2006/043895 A1 | 4/2006 |
| WO | 2007/094254 A1 | 8/2007 |
| WO | 2008/033788 A2 | 3/2008 |
| WO | 2008/064242 A2 | 5/2008 |
| WO | 2008/071351 A1 | 6/2008 |
| WO | 2008/120021 A1 | 10/2008 |
| WO | 2009/017614 A1 | 2/2009 |
| WO | 2009/073567 A1 | 6/2009 |
| WO | 2009/157852 A1 | 12/2009 |
| WO | 2010/084432 A1 | 7/2010 |
| WO | 2010/094249 A1 | 8/2010 |
| WO | 2011/161609 A1 | 12/2011 |

OTHER PUBLICATIONS

French Search Report dated Feb. 9, 2009 in co-pending French patent application No. 0853629.
European communication dated May 17, 2010 in co-pending European patent application No. 10290005.7.
French Search Report dated Oct. 16, 2009 in co-pending French Patent Application No. 0950435.
Chinese Communication, with English translation, dated Sep. 27, 2012 in co-pending Chinese patent application No. 201010004496.1.
International Search Report and Written Opinion dated May 7, 2010 in co-pending PCT application No. PCT/IB2010/050102.
International Preliminary Report on Patentability dated Aug. 4, 2011 in co-pending PCT application No. PCT/IB2010/050102.
French Search Report dated Sep. 24, 2010 in co-pending French patent application No. 1050209.
French Search Report dated Nov. 25, 2010 in co-pending French patent application No. 1054514.
Korean communication, with English translation, dated Jul. 31, 2014 in co-pending Korean patent application No. 10-2013-7000355.
European communication dated Sep. 18, 2017 in co-pending European patent application No. 11746615.1
French Search Report dated Nov. 12, 2010 in co-pending French patent application No. 1055025.
Korean communication, with English translation, dated Jul. 31, 2014 in co-pending Korean patent application No. 10-2013-7001692.
French Search Report dated Feb. 3, 2011 in co-pending French patent application No. 1055026.
French Search Report dated May 24, 2011 in co-pending French patent application No. 1056421.
European communication dated Apr. 6, 2010 in co-pending European patent application No. 09290938.1.
French Search Report dated Nov. 22, 2010 in corresponding French patent application No. 1054517.
Korean communication, with English translation, dated Jul. 31, 2014 in corresponding Korean patent application No. 10-2013-7000366.
European communication dated Sep. 18, 2017 in corresponding European patent application No. 117286801.
French Search Report dated Nov. 22, 2010 in co-pending French patent application No. 1054516.
Korean communication, with English translation, dated Jul. 31, 2014 in co-pending Korean patent application No. 10-2013-7000356.
French Search Report dated Nov. 17, 2011 in co-pending French patent application No. 1152556.
International Search Report dated Jun. 8, 2011 in co-pending PCT Application No. PCT/IB2011/050089.
Written Opinion of the International Searching Authority dated Jun. 8, 2011 in co-pending PCT application No. PCT/IB2011/050089.
International Preliminary Report on Patentability dated Jul. 26, 2012 in co-pending PCT application No. PCT/IB2011/050089.
International Search Report and Written Opinion dated Sep. 30, 2011 in co-pending PCT Application No. PCT/IB2011/052447.
International Preliminary Report on Patentability dated Dec. 20, 2012 in co-pending PCT application No. PCT/IB2011/052447.
International Search Report dated Sep. 29, 2011 in co-pending PCT Application No. PCT/IB32011/052676.
Written Opinion of the International Searching Authority dated Sep. 29, 2011 in co-pending PCT application No. PCT/IB2011/052676.
International Preliminary Report on Patentability dated Jan. 10, 2013 in co-pending PCT application No. PCT/IB2011/052676.
International Search Report dated Aug. 29, 2011 in co-pending PCT Application No. PCT/IB2011/052679.
Written Opinion of the International Searching Authority dated Aug. 29, 2011 in co-pending PCT application No. PCT/IB2011/052679.
International Preliminary Report on Patentability dated Jan. 10, 2013 in co-pending PCT application No. PCT/IB2011/052679.
International Search Report dated Aug. 2, 2011 in corresponding PCT Application No. PCT/IB2011/052448.
Written Opinion of the International Searching Authority dated Aug. 2, 2011 in corresponding PCT application No. PCT/IB2011/052448.
International Preliminary Report on Patentability dated Dec. 20, 2012 in corresponding PCT application No. PCT/IB2011/052448.
International Search Report and Written Opinion dated Sep. 28, 2011 in co-pending PCT Application No. PCT/IB2011/052450.

(56) References Cited

OTHER PUBLICATIONS

International Preliminary Report on Patentability dated Dec. 20, 2012 in co-pending PCT application No. PCT/IB2011/052450.
International Search Report dated Sep. 4, 2012 in co-pending PCT application No. PCT/IB2012/051424.
International Search Report and Written Opinion dated Nov. 8, 2013 in co-pending PCT application No. PCT/IB2013/055926.
International Preliminary Report on Patentability dated Feb. 5, 2015 in co-pending PCT application No. PCT/IB2013/055926.
International Search Report and Written Opinion dated Dec. 5, 2013 in copending PCT application No. PCT/IB2013/055925.
International Preliminary Report on Patentability dated Feb. 5, 2015 in co-pending PCT application No. PCT/IB2013/055925.
Millipore, "Process Containers," published at <http://www.millipore.com/bioproduction/bp3/containers>, available on Apr. 5, 2008, 2 pages.
Office action dated Mar. 9, 2016 in co-pending U.S. Appl. No. 13/872,248.
Final rejection dated Jun. 16, 2016 in co-pending U.S. Appl. No. 13/872,248.
Office action dated Nov. 2, 2016 in co-pending U.S. Appl. No. 13/872,248.
Final rejection dated Feb. 8, 2017 in co-pending U.S. Appl. No. 13/872,248.
Advisory action dated Apr. 18, 2017 in co-pending U.S. Appl. No. 13/872,248.
Office action dated Jun. 8, 2017 in co-pending U.S. Appl. No. 13/872,248.
Final rejection dated Oct. 17, 2017 in co-pending U.S. Appl. No. 13/872,248.
Office action dated Jul. 23, 2018 in co-pending U.S. Appl. No. 15/161,768.

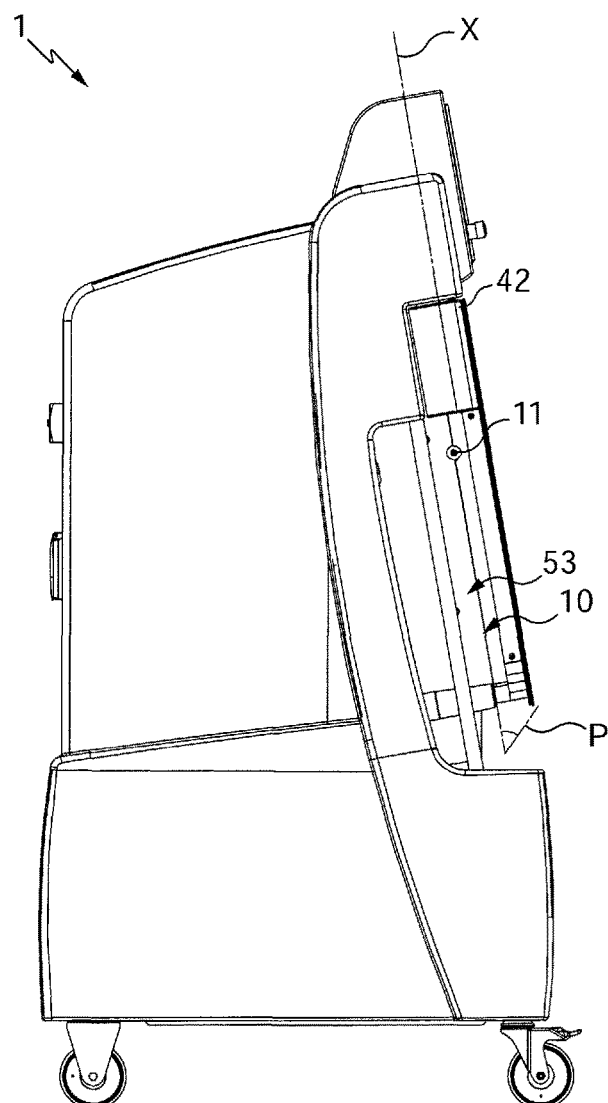
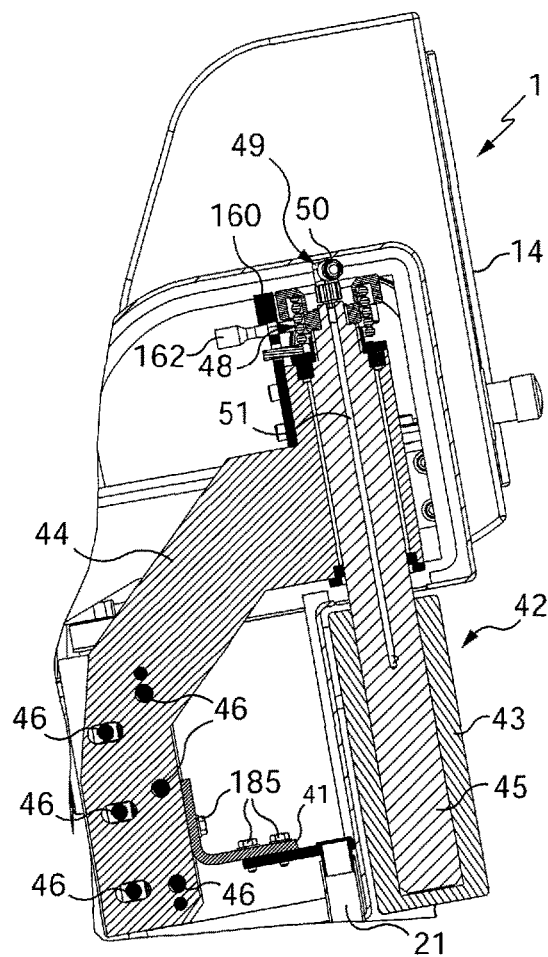
Fig. 4
Fig. 5

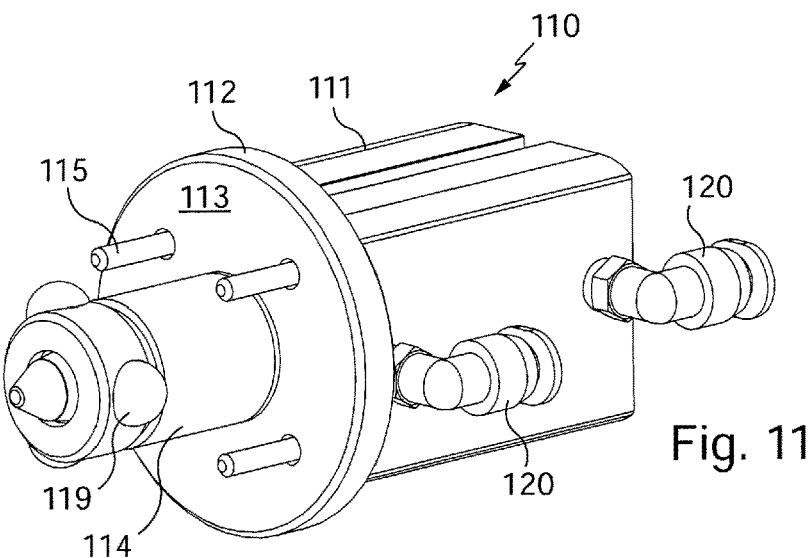
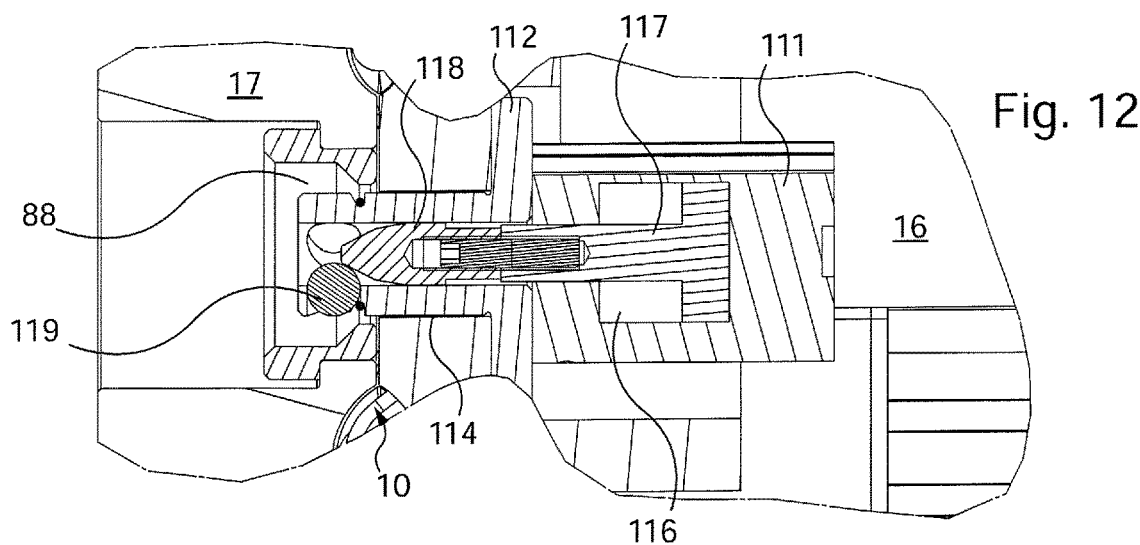
Fig. 11
Fig. 12
Fig. 13

DEVICE FOR A BIOLOGICAL LIQUID TREATMENT INSTALLATION

This application is a continuation of U.S. patent application Ser. No. 13/872,248 filed Apr. 29, 2013, the disclosure of which is hereby incorporated by reference, which is a divisional of U.S. patent application Ser. No. 13/153,804, filed Jun. 6, 2011 (now U.S. Pat. No. 9,205,955 issued Dec. 8, 2015), which claims priority of French Patent Application No. 1054517 filed Jun. 8, 2010.

The invention relates to a device for a biological liquid treatment installation, particularly but not exclusively, for purifying a biopharmaceutical liquid in order to obtain products such as monoclonal antibodies, vaccines or recombinant proteins.

It is known that biopharmaceutical liquids are in general obtained by culture in a bioreactor and that they must then be treated to achieve the required characteristics of purity, concentration, absence of viruses, etc.

The purification is carried out by means of a succession of treatments such as clarification, to eliminate the residues from the bioreactor culture, and viral filtration sometimes followed by diafiltration and concentration by tangential flow filtration (TFF). Other operations exist concerning purification, such as chromatography.

A number of types of container containing liquids can be connected to the inlet of the circuit, such as the source container that contains the product to be treated, but also the containers containing a cleaning liquid such as sodium hydroxide, a rinsing liquid such as pure water or a buffer liquid such as a saline solution. In addition to the container for collecting the treated liquid, various other containers for collecting cleaning, rinsing or buffer liquid, or for collecting residues, can be connected to the outlet of the circuit.

In a production context the liquid treatments can be carried out sequentially, the collecting container for the first treatment potentially becoming the source container for the next treatment, and so on until the last treatment is carried out.

These treatments are conventionally carried out in dedicated installations comprising stainless steel pipes and other parts such as tanks or filter housings, which necessitate operations before and after the actual treatment, which are relatively onerous, in particular operations of cleaning after use.

Within the last few years, these treatments have alternatively been carried out in installations in which the components in contact with the liquid are single-use components.

The invention aims to provide a device enabling the simple, economical and convenient implementation of treatments for biological liquid.

For this, the invention concerns a device for an installation for biological liquid treatment comprising:
- a base having a front face;
- a moveable or removable door, said device having a closed door position;
- in the closed door position, a circuit comprising a plurality of connectors and a network for conveying liquid between said connectors, which circuit comprises a bag comprising two flexible films and said conveying network connectors, which circuit further comprises a press comprising a first shell disposed on said front face of said base and a second shell disposed in said door; and
- a hinge system hinging said door relative to said base, said hinge system being disposed only on one side of said door so as to form, in the closed door position, lateral clearances between said door and said base over the rest of a perimeter of said door, so as to enable free access to the connectors of said bag.

By virtue of the invention, it is possible to very simply and rapidly connect the connectors of the bag of the circuit to surrounding treatment components.

To be precise, in addition to the device according to the invention, the biological liquid treatment installation comprises, depending on the treatments carried out, one or more other devices, for example juxtaposed to the device according to the invention.

This or these other device or devices is or are provided with those above-mentioned surrounding treatment components, formed in particular by one or more pumps, for example of the diaphragm type, and/or by a source container containing the product to treat and/or by a treated liquid collecting container and/or by a chromatography column, these surrounding treatment components each being connected to the bag, directly or not.

By virtue of the arrangement of the hinge system enabling the hinging of the door relative to the base on one side only of the door, lateral clearances are advantageously formed over a major part of the outer perimeter of the door, between that door and the base.

Thus, the bag of the circuit may comprise connectors emerging to the exterior of a major part of its outline with free access thereto by virtue of the lateral clearances, to connect pipes thereto coming from the surrounding treatment components (pump(s) and/or container(s) and/or column).

Moreover, by virtue of the lateral clearances formed according to the invention, the routing of the pipes which connect the circuit to the surrounding treatment components is simplified, while avoiding the pipes passing in front of the door.

By virtue of the invention, it is also possible to change the bag very simply and very rapidly and if necessary the first shell and the second shell so as to perform a new treatment, whether of the same type or a different type.

To be precise, for this it suffices to actuate the passage from the closed door position to the other position, that is to say to open or remove the door from the device, to remove the bag, before or after having disconnected tubes coming from surrounding treatment components and that were connected beforehand onto connectors emerging from the bag, then, if necessary, to remove the first and second shells respectively from the base and from the door. Lastly, it suffices to install in the device first and second shells as well as a bag for the second treatment, to control the passage from the other position to the closed door position, and to connect tubes to the connectors emerging from the bag.

Where the door is moveable relative to the base, it suffices first of all to open it then close it again on the base.

Where the door is removable, it suffices first of all to remove it then to put it back on the base.

In this way, it is possible to pass from a first treatment, for example a treatment by tangential filtration, to a second treatment of another type, for example a treatment by chromatography, in a simple, economical, convenient and efficient manner.

Of course, where the following treatment is different from the previous one, the bag and the first and second shells for the second treatment have features (conduits of the conveying network, connectors) that are different from the bag and the first and second shells for the previous treatment, so as to form a circuit adapted to the following treatment.

The invention furthermore makes it possible to have a device provided with a base and a single door for carrying out different types of treatments, by virtue of a modular circuit of which the modules (bag, first shell and second shell) are interchangeable depending on the treatments carried out.

Optionally, said hinge system comprises a single hinge disposed at a corner of said door, and said hinge comprises a first hinge portion fastened to said corner of said door and a second hinge portion fastened to a lateral face of said device, which lateral face is connected to said front face.

Also optionally, the axis of said hinge is offset from a joining plane formed between said first shell and second shell in the closed door position.

According to preferred, simple, convenient and economical features of the device according to the invention:

said base of said device comprises, on its front face, a console-forming inclined chassis on which is disposed the first shell, which chassis comprises hooking claws, and the first shell comprises dowels engaged in said hooking claws;

said device comprises a first locking system for fastening said second shell into a frame of said door, which first locking system comprises:

at least one jack disposed in said frame;

at least one spring disposed in said frame;

at least one rod linked to said at least one jack by a first end and to at least one spring by a second end that is an opposite end to the first end, said at least one rod comprising at least one locking bolt and having an unlocked position and a locked position; and at least one lock strike arranged in a recess of said second shell;

said at least one jack being configured to actuate the passage of said at least one rod between its locked position and its unlocked position;

said at least one spring being configured to actuate the passage of said at least one rod between its unlocked position and its locked position; and said at least one locking bolt being engaged in said at least one lock strike in the locked position of said rod and being disengaged from said at least one lock strike in the unlocked position of said rod;

said device comprises a second locking system configured such that it locks together said first shell and said second shell when said door is in the closed door position;

said second shell has a first hole, said bag comprises at least one second through aperture in a treatment zone of said liquid, and said second locking system comprises at least one ball-lock pin provided with a body, a head and balls and having an unlocked state and a locked state, said ball-lock pin being fastened to said first shell, said head passing through said first shell and said second through aperture and emerging into said first hole of said second shell in the closed door position, said balls entering said head in said unlocked state of said pin and projecting from said head in said locked state of said pin;

said circuit comprises instruments necessary for the treatment of said biological liquid, in particular valves to allow or prevent the passage of said liquid in said conduits, and/or sensors of physico-chemical values of said liquid, and said instruments are integrated into said first shell;

said first shell comprises a first connector at the back, and said base of said device comprises a second connector configured such that it connects to said first connector to power said instruments integrated into said first shell;

said front face of said base comprises a frame provided with an opening, and said second connector is configured such that it passes through said opening to connect to said first connector;

in the closed door position, said bag is clamped between the first and second shells in a state in which conduits of said network for conveying liquid are formed between said films.

said device has a position other than said closed door position in which said bag is carried only by the first shell;

the two said flexible films of said bag are joined to each other and delimit a zone for treatment of said liquid according to a closed outline, said conveying network connectors emerging on the inside and on the outside of at least one side of said outline;

said bag comprises first through apertures on a side of said bag for its positioning, and said first shell comprises studs for hooking said bag which pass through said first through apertures of said bag; and said bag comprises at least one third through aperture on a side of said bag, said first shell comprises at least one dowel and said second shell comprises at least one second hole, wherein, in the closed door position, said at least one dowel passes through said third through aperture of said bag and said at least one second hole receives said dowel of said first shell.

The disclosure of the invention will now be continued with the description of embodiments, given below by way of illustrative and non-limiting example, with reference to the accompanying drawings, in which:

FIG. 4 is a view from the left side of the device, in closed door position;

FIG. 5 is a partial cross-section view showing a hinging system linking the door to a base of the device;

FIG. 11 is an isolated perspective view of the system for locking the first and second shells together;

FIGS. 12 and 13 are cross-section views partially showing the first and second shells, with the locking system respectively in an unlocked and in a locked state;

FIGS. 1 and 2 illustrate a device 1 for a biological liquid treatment installation (not shown).

Figure 1:
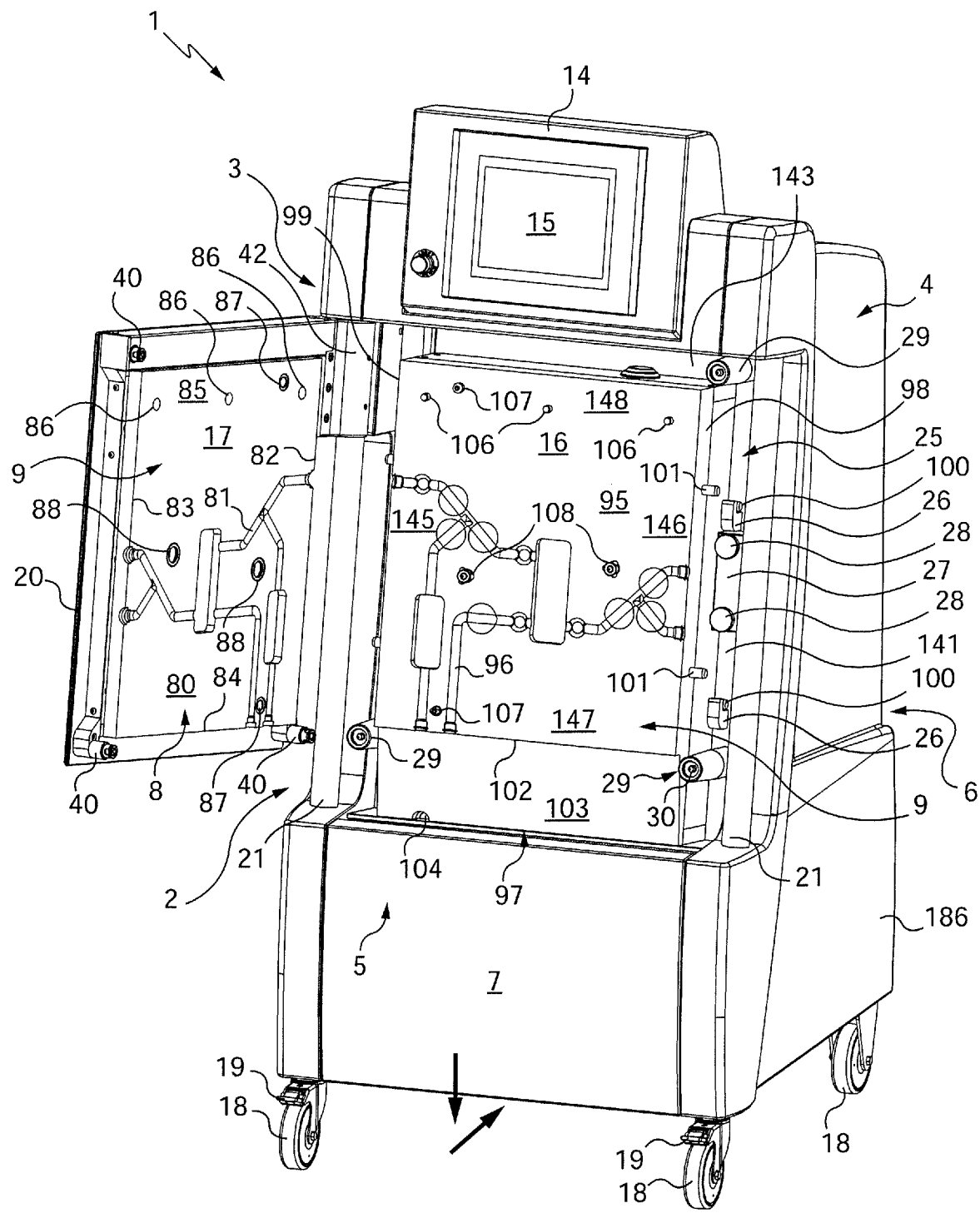
FIG. 1 is a perspective view of a device for a biological liquid treatment installation according to a first embodiment example of the invention, without the bag.

The device 1 is of generally parallelepiped form.

This device 1 comprises a base 2 having a first lateral face 3, a second lateral face 4 which is an opposite face to the first lateral face 3, a front face 5 meeting the first and second lateral faces 3 and 4, and a back face 6 which is an opposite face to the front face 5 and which meets the first and second lateral faces 3 and 4.

Figure 2:
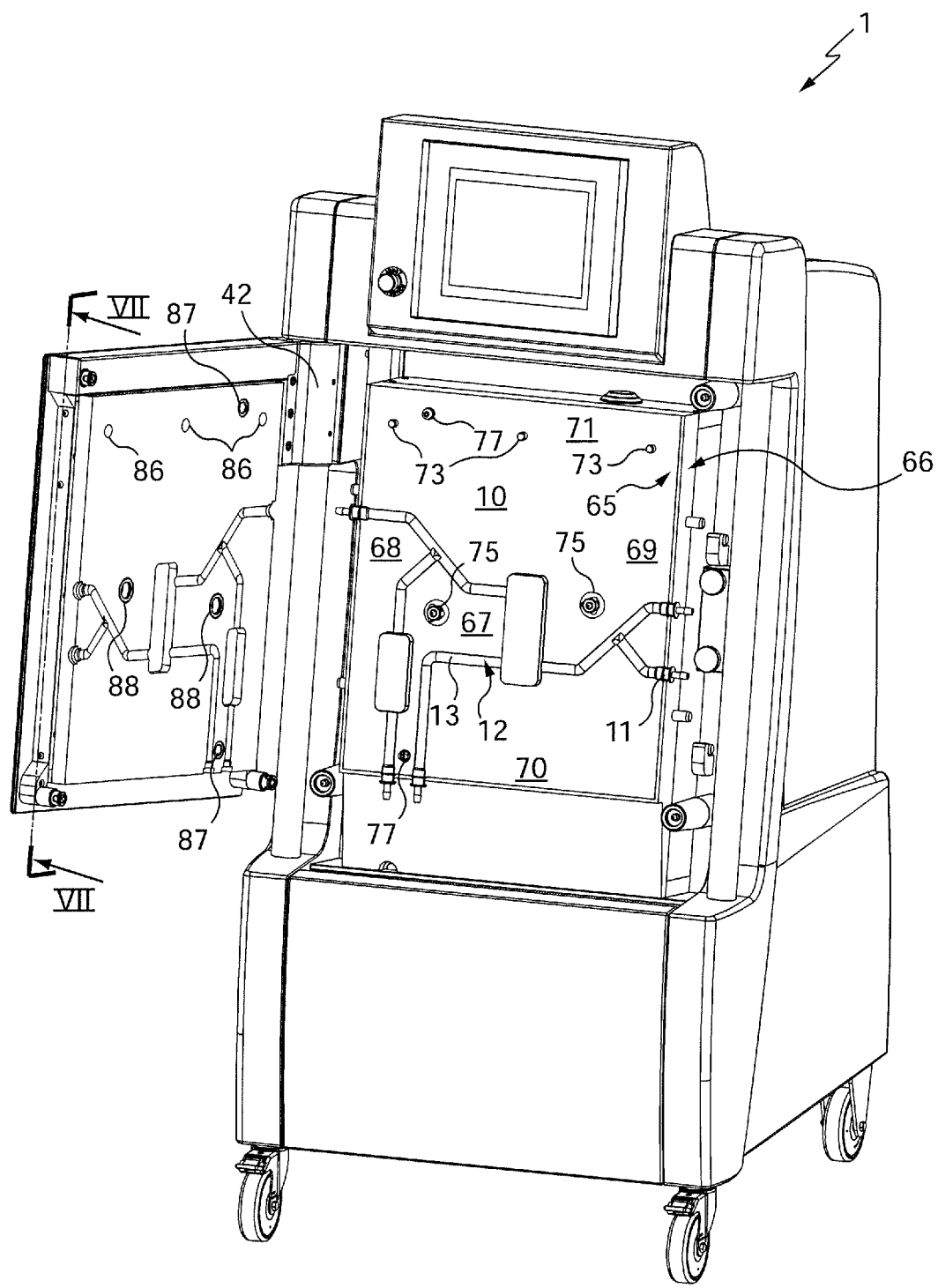
FIG. 2 is a similar view to FIG. 1, with the bag.

The device 1 further comprises a circuit 8 provided with a press 9 and a bag 10, which comprises a plurality of connectors 11 for liquid and a network 12 for conveying liquid between those connectors 11 of which the conduits 13 can be seen in FIG. 2.

The press 9 comprises two shells 16 and 17 each formed from a solid block of rigid material.

Here, the shells 16 and 17 are of polyoxymethylene (POM), also called acetal, and each has a generally parallelepiped form.

The shell 16 is mounted on the front face 5 of the base 2.

The device 1 further comprises a door 20 hinged to the base 2.

The shell 17 is mounted in that door 20.

The device 1 has a closed door position in which the door 20 is closed and covers the shell 16, and another position in which the bag 10 is carried only by the shell 16.

In this other position, the shell 17 is away from the shell 16.

In the closed door position, the bag 10 is inserted between the two shells 16 and 17.

The device 1 is provided, at the bottom, with a closed bay 186 intended to receive one or more tanks (not shown) comprising a sachet, which tanks form for example a container for collecting treated liquids or a waste container.

This bay 186 is closed by a sliding panel 7 disposed on the front face 5 of the device 1, which panel 7 is adapted to be moved in translation downwardly then towards the back of the device 1 (see the arrows in FIG. 1) so as to insert and withdraw the tanks.

A control panel 14 is arranged at the top of the front face 5 of the device 1.

This control panel 14 is provided with a graphical touch interface 15 enabling the biological liquid treatment process to be verified and controlled.

This control panel 14 is thus arranged at a height enabling a user to make use of it.

In order to make it easier to move, the device 1 is in the form of a cart mounted on four castors 18 (of which three can be seen in FIG. 1), with two castors situated under the front face of the device 5 which comprises a brake 19, and with the device 1 furthermore having two handles 21 on respective opposite sides of the front face 5, in the vicinity of the respective lateral faces 3 and 4.

The device 1 comprises a chassis 25 at its front face 5.

Figure 3:
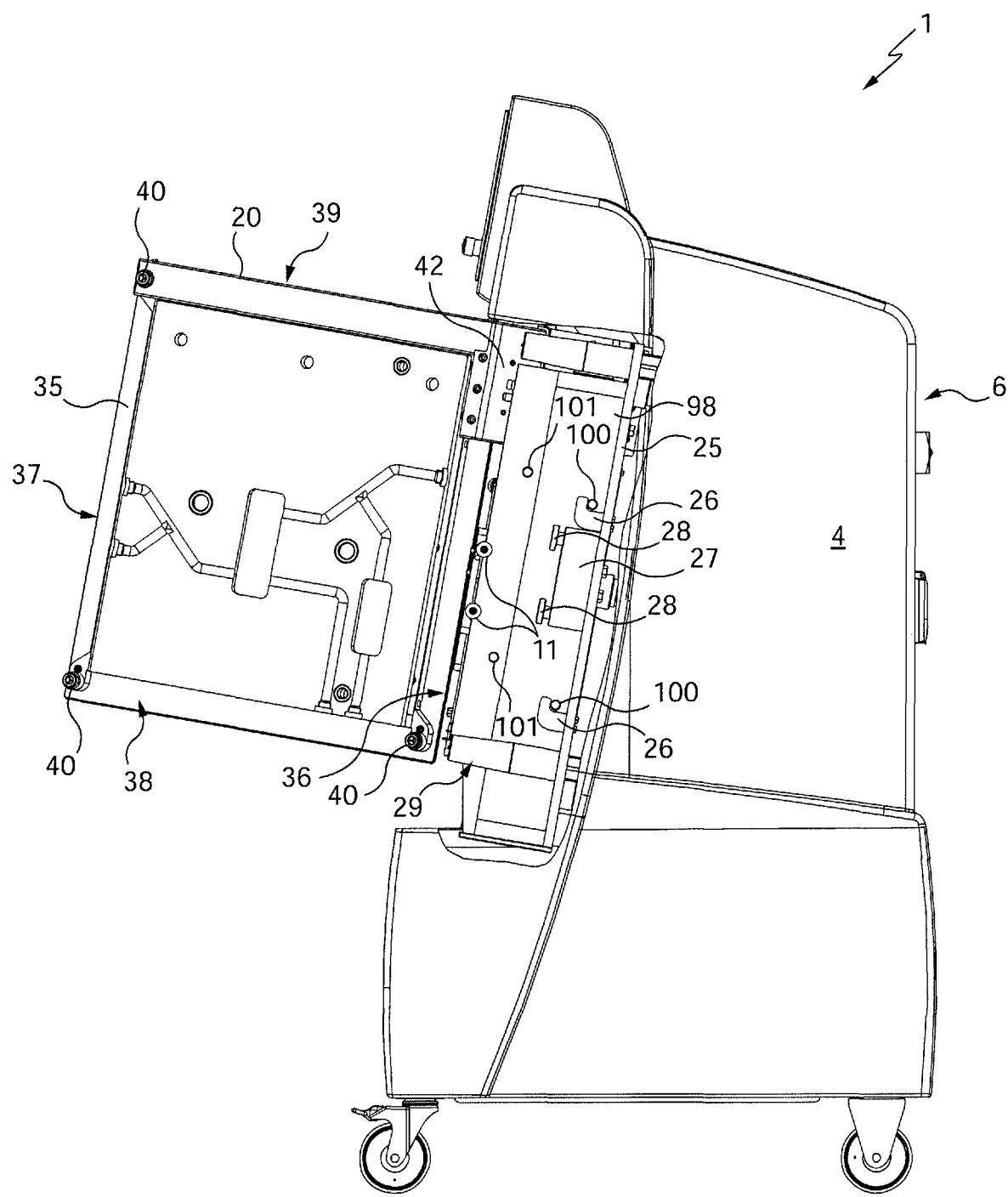
FIG. 3 is a view from the right side of the device, with a right lateral panel partially torn away.

As can be seen more particularly in FIG. 3, this chassis 25 is inclined.

The chassis 25 has an outer perimeter and an inner perimeter that are delimited by four sides, of which a left side 140 (visible in FIG. 16) and a right side 141 which are opposite sides, and a top side 143 and a bottom side 142 (visible in FIG. 16) which are opposite sides.

The left 140 and right 141 sides each comprise two superposed L-shaped hooking claws 26 emerging from the respective side and extending upwardly.

A support plate 27 is fastened to the right side 141 of the chassis 25, between the two hooking claws 26.

This support plate 27 is disposed in the immediate vicinity under the hooking claw 26 situated higher on the right side 141, so as to leave free access to the hooking claw 26 situated lower down on that same right side 141.

The support plate 27 comprises two fastening heads 28 on which a platform (not shown) is adapted to be fastened so as to dispose thereon instruments that may be necessary for the treatment of the biological liquid.

These instruments may for example be optional kits such as sensors measuring pH or conductivity and are chosen by the user according to the type of treatment to carry out.

The base 2 of the device 1 further comprises devices 29 which, with complementary devices 40 of the door 20, enable the positioning and the locking of that door 20 in the closed door position.

There are three of the devices 29, which are situated at the corners of the chassis 25, respectively at top right, bottom right, and bottom left, as can be seen particularly in FIGS. 1 and 2.

These devices 29 each comprise a body, an annular shoulder (not shown), a head connected to that annular shoulder, that head having the form of a conical tube (FIGS. 1 and 2) and being provided internally with a rod 30 with a conical tip. The body comprises a pneumatic chamber, a piston that is mechanically linked to the rod 30 with a conical tip, which rod 30 is adapted to extend within the head.

As can be seen in FIGS. 1 to 3, the door 20 comprises a frame 35 having a generally rectangular outline.

This frame 35 has a first side 36, a second side 37 that is an opposite side to the first 36, a third side 38 meeting the first and second sides 36 and 37 and a fourth side 39 that is an opposite side to the third side 38 and that meets the first and second sides 36 and 37.

The frame 35 comprises three complementary devices 40 adapted to cooperate with the devices 29 of the base 2, which complementary devices 40 are respectively situated at the upper left, bottom left, and bottom right corner, as can be seen in FIGS. 1 to 3.

Figure 16:
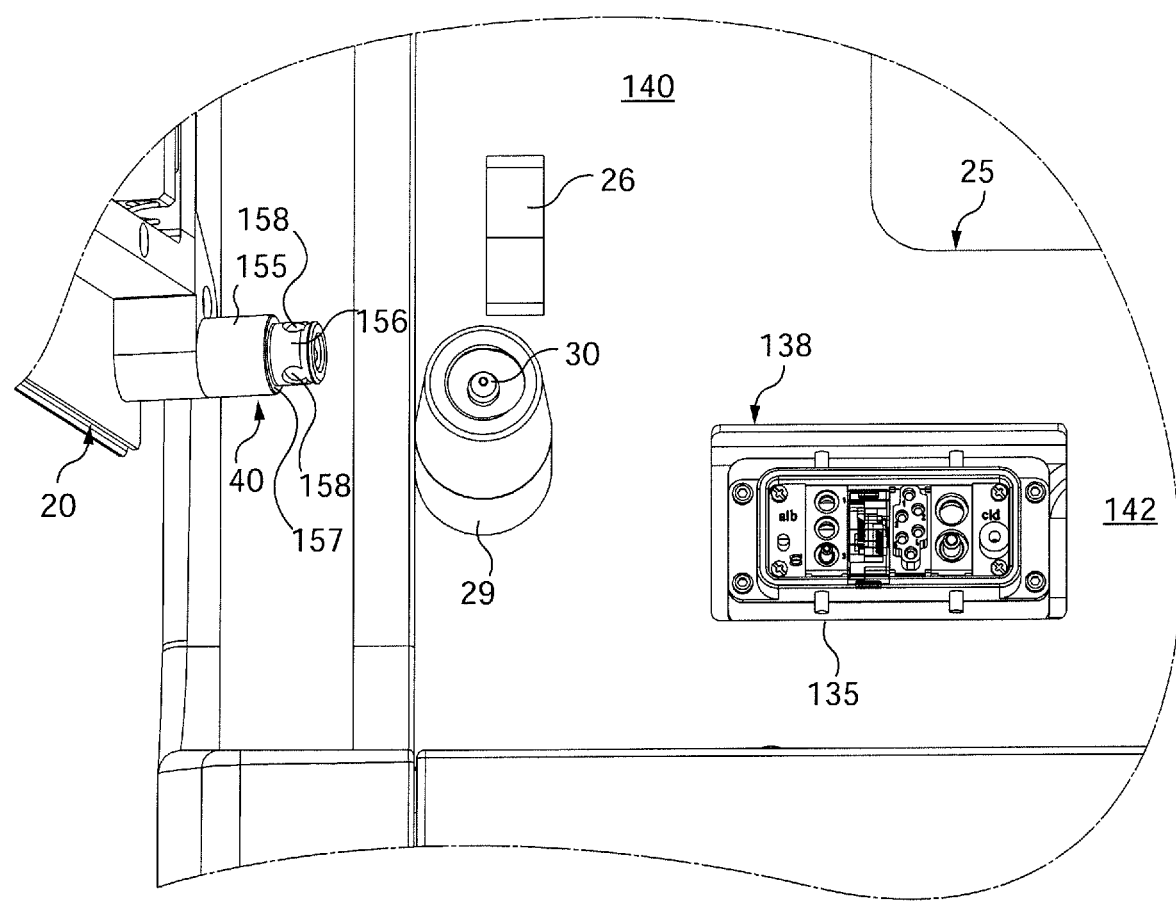
FIG. 16 is a partial view from the font of the device, with the first shell removed.

These complementary devices 40 are provided with a first cylindrical portion 155 and a second cylindrical portion 156 that is hollow and connected to the first portion 155 by a shoulder 157 (FIG. 16). This second portion 156 is of smaller diameter than the diameter of the first portion 155. Furthermore, the second portion 156 is provided with three apertures 158 on its outer surface.

These complementary devices 40 further comprise three balls (not shown) each able to project from the second portion 156 by passing through a respective aperture 158.

In the closed door position, each second portion 156 of a respective complementary device 40 of the door 20 is inserted into a respective head of a respective device 29 of the base 2.

The devices 29 and complementary devices 40 form, in pairs, a ball-lock pin system provided with a pneumatic jack of double-acting type with a spring (not shown), having an extended position and a retracted position, the operation of which is well-known.

The rod 30 of the device 29 is adapted to be introduced into the hollow second cylindrical portion 156 when the jack is in its extended position.

In this position of the jack, the rod 30 pushes the balls until each of them passes through an aperture 158, so blocking movement of door 20 relative to the base 2.

The device 1 further comprises a hinge system by virtue of which the door 20 is hinged to the base 2.

This hinge system is provided with a single hinge 42 comprising a first hinge portion 43 fastened to the top right corner of the frame 35 of the door 20, and a second hinge portion 44 fastened to the lateral face 3 of the base 2 of the device 1.

Figure 6:
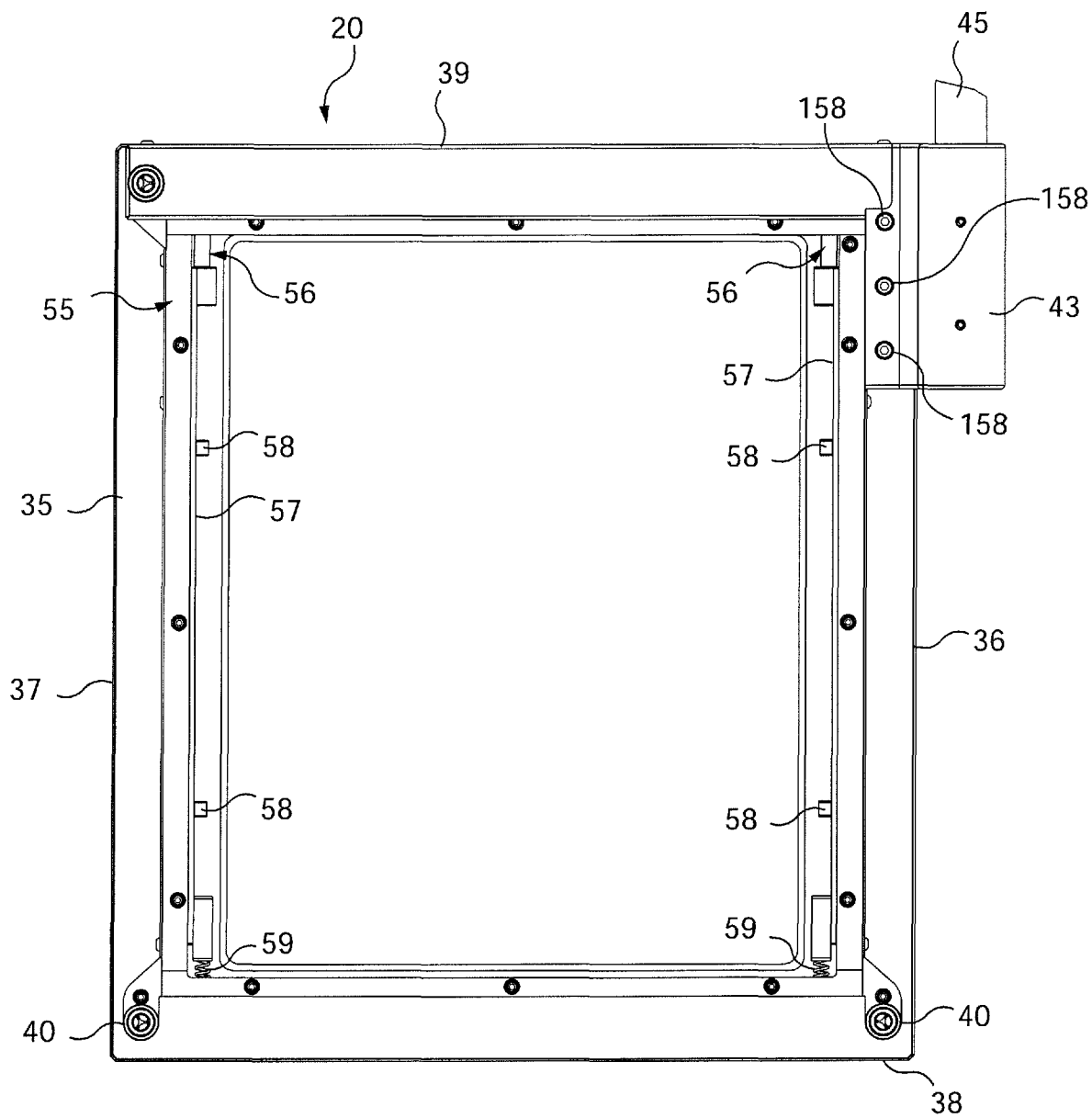
FIG. 6 is a view of the interior of the door, in isolation, without the second shell, and showing the locking system of that second shell in that door.

The hinge portion 43 is fastened to the first side 36 of the frame 35 via three fastening screws 158 (FIG. 6).

As can be seen in more detail in FIG. 5, the hinge portions 43 and 44 respectively of the door 20 and of the base 2 are joined together by a rod 45 forming a pivotal link.

The hinge portion 44 of the base 2 is fastened via six fastening screws 46 to the lateral face 3 of the base 2.

An adjusting shim (not shown) situated behind that hinge portion 44 enables the latter to be adjusted as well as possible.

Furthermore, at the bottom of FIG. 5 it can be seen that the handle 21 is indirectly fastened to that hinge portion 44 via a bent plate 41 and fastening screws 185.

On the upper part of the hinge portion 44 a mechanical spring 48 is arranged with a plastic stop 160 to facilitate the opening and closing of the door 20.

The device also includes a position sensor 162 to verify and provide security for the opening and closing of the door 20, by detecting the closed door position and the other position.

A pneumatic system 49 is also arranged on the upper part of the hinge portion 44 so as to supply a system (described later) for locking the shell 17 and which is situated in the door 20.

For this, that system 49 comprises a connector 50 connected both to the pneumatic power supply (not shown) and to an aperture 51 formed in the rod 45, which aperture 51 extends in the rod 45 from the connector 50 to the hinge portion 43 which is in the door 20.

In the closed door position, as is illustrated more particularly in FIG. 4, the rotational axis X about which the hinge portion 43 of the door 20 pivots is offset relative to a parting surface P formed between the shells 16 and 17 when they clamp the bag 10 between them.

This axial offset towards the front of the device 1 of the axis X relative to the parting surface P enables lateral clearances 53 to be formed between the door 20 and the base 2 at the outer perimeter of the door 20.

Thus, the access for example to the connector 11 of the bag 10 illustrated in FIG. 4 is greatly facilitated.

The door 20 further comprises, in its frame 35, a system 55 for locking the shell 17 (FIG. 6).

This system 55 comprises two jacks 56 disposed on respective opposite sides of the frame 35, on its top portion, and rods 57 which extend over a major portion of the height of the frame 35.

The jacks 56 are of single-acting pneumatic type with a spring, which is not integrated into the jack 56, and are supplied by the connector 50 which can be seen in FIG. 5.

These jacks 56, as will be seen in more detail below, are each connected to a rod 57 and are each adapted to push that rod 57 between a locked position and an unlocked position of the system 55.

Each rod 57 comprises two locking bolts 58.

The system 55 further comprises two springs 59 disposed in the bottom of the frame 35, each spring 59 being connected to a rod 57 to push that respective rod 57 into its locked position and thus advance the corresponding locking bolt 58.

Figure 20:
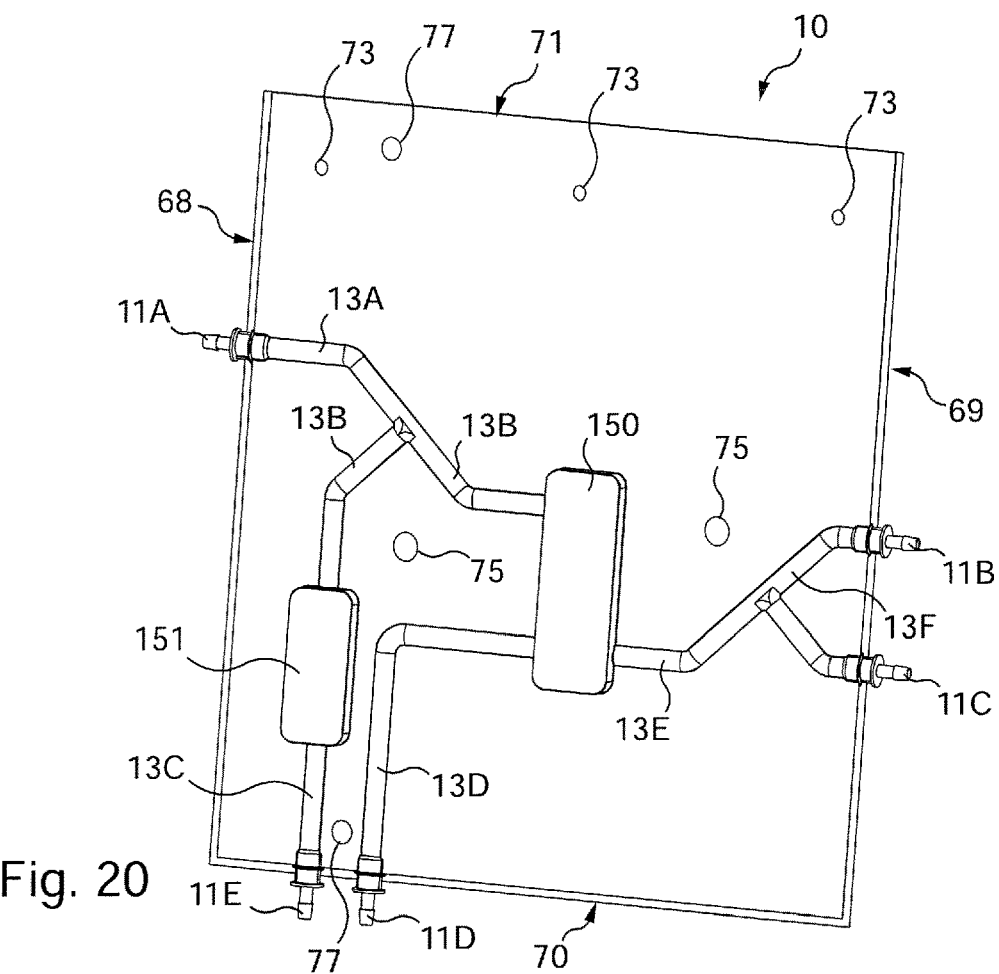
FIG. 20 is a perspective view of the bag.

The bag 10 comprises two flexible films 65 and 66 connected to each other by a seal delimiting a closed contour, and the connectors 11 of the conveying network 12 (FIGS. 2 and 20).

Thus, each of the films 65 and 66 is a PureFlex™ film from the applicant.

This is a co-extruded film comprising four layers, respectively, from the inside to the outside, a layer of ultra low density polyethylene (ULDPE) forming the material for contact with a liquid, a copolymer of ethylene and vinyl alcohol (EVOH) forming a barrier to gases, a copolymer layer of ethylene and vinyl acetate (EVA) and a layer of ultra low density polyethylene (ULDPE) forming the outer layers.

The seal is a weld bead formed at the periphery of the films 65 and 66.

In addition to the films 65 and 66 and the connectors 11 for liquid, the bag 10 comprises a connector for an pneumatic agent (not shown) to form the conduits 13 (13A to 13F in FIG. 20).

The closed contour of the bag 10 forms a liquid treatment zone 67, in which extend the conduits 13.

The closed contour has a first side 68, a second side 69 that is an opposite side to the first 68, a third side 70 meeting the first and second sides 68 and 69 and a fourth side 71 that is an opposite side to the third side 70 and that meets the first and second sides 68 and 69. The connectors 11 of the conveying network 12 emerge inside and outside the first, second, and third sides 68, 69, and 70, as can be seen more particularly in FIG. 20.

The dimensions of the bag 10 correspond to those of the surfaces of the shells 16 and 17.

As will be seen below, the bag 10 is provided for clamping between by the shells 16 and 17 with one of the faces of the bag 10 in contact with the face of the shell 16, and with the other face of the bag 10 being in contact with a face of the shell 17.

At its fourth side 71, the bag 10 further comprises three through apertures 73 for positioning.

These positioning apertures 73 are aligned and regularly spaced apart, two of the apertures 73 being situated on respective opposite sides of the fourth side 71 of the bag 10, and the other aperture 73 being situated in the center of the fourth side 71 of the bag 10.

These positioning apertures 73, as will be seen below, serve for the positioning of the bag 10 on the shell 16.

The bag 10 further comprises, in its treatment zone 67, two through apertures 75 for locking the shells 16 and 17 together, these locking apertures 75 having a greater diameter than the positioning apertures 73.

These locking apertures 75 are situated in the treatment zone 67 at the locations where there are the most conduits 13, since it is at these locations where the force of pressure is greatest during the treatment. The locking apertures 75 are thus at least partially surrounded by conduits 13.

It will be seen below how means for locking the shells 16 and 17 together perform this locking and at the same time clamp between them the bag 10 in the circuit 8.

The bag 10 further comprises other positioning apertures 77.

One of the positioning apertures 77 is situated at the fourth side 71 of the bag 10 in the vicinity of the positioning aperture 73 situated at the top left of the bag 10, and the other positioning aperture 77 is situated at the opposite extreme, that is to say towards the bottom of the bag 10, in the treatment zone 67.

These positioning apertures 77, as will be seen below, serve for the positioning of the door 20 in the closed door position of the device.

As can be seen in FIGS. 1 to 3, the shell 17 has a reference surface 80, which is flat here, and a plurality of shaping channels 81 recessed into that reference surface 80. This shell 17 has a first side 82 and a second side 83 that is an opposite side to the first side 82, a third side 84 and a fourth side 85 that is an opposite side to the third side 84, these third and fourth sides 84 and 85 each meeting the first and second sides 82 and 83.

On its fourth side 85, the shell 17 is provided with three positioning holes 86 for positioning the bag 10, which are arranged, as will be seen below, facing the positioning apertures 73 of the bag 10 in the closed door position, with bag 10 clamped between the shells 16 and 17.

Furthermore, the shell 17 is provided with two other positioning holes 87 for positioning the door 20 in the closed door position, one of which is situated at the first side 82 of the shell 17, and the other at the other extreme, towards the bottom of the shell 17.

As will be seen below, these two positioning holes 87 are arranged so as to face the positioning apertures 77 of the bag 10 in the closed door position, with the bag 10 clamped between the shells 16 and 17.

In a central zone, the shell 17 further comprises two other locking holes 88 of greater diameter than the positioning holes 86 and 87 of that shell 17, which locking holes 88 serve for the locking together of the shells 16 and 17 as will be seen below.

These locking holes 88 are situated at the locations where there are the most channels 81 serving for the formation of the conduits 13, since it is at these locations that the force of pressure is greatest during the treatment. The locking holes 88 are thus at least partially surrounded by channels 81.

As will be seen below, these locking holes 88 are arranged so as to face the locking apertures 75 of the bag 10 in the closed door position, with the bag 10 clamped between the shells 16 and 17.

Figure 7:
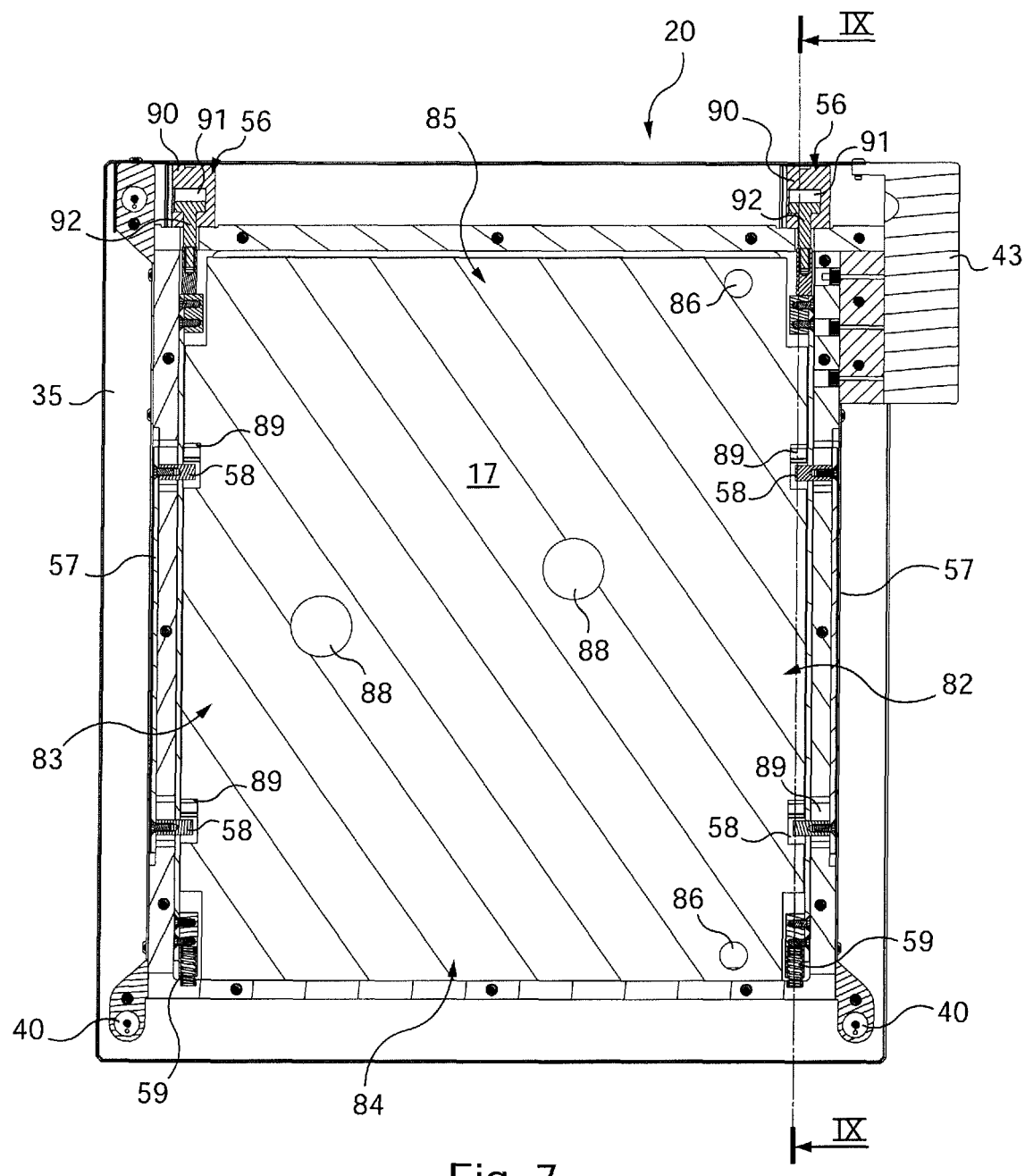
FIGS. 7 and 8 are cross-section views on VII-VII of FIG. 2, showing the locking system of the second shell in the door, respectively in an unlocked and in a locked state.
Figure 10:
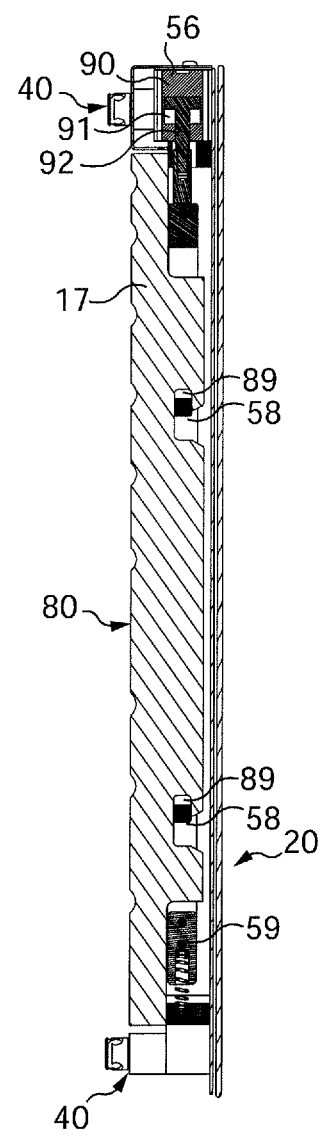

As shown by FIGS. 7 and 10, the shell 17 is provided with four lock strikes 89 each formed in a recess of the body of the shell 17.

Two lock strikes 89 are arranged along the first side 82 of the shell 17, and two other lock strikes 89 are arranged along the second side 83 of the shell 17, that is to say that the four lock strikes 89 are in opposite pairs.

As stated previously, the shell 17 is fastened into frame 35 of door 20, and the locking of that shell 17 into the door 20 will be described with reference to FIGS. 7 to 10.

Each jack 56 is provided with a body 90 comprising a pneumatic chamber 91 and a moveable piston 92 extended by a rod, which jack is housed in the frame 35 of the door 20, each piston 92 having an extended position and a retraced position in which the piston 92 has been moved through a predetermined travel relative to its extended position.

Each jack 56 is pneumatically connected to the aperture 51 formed in the rod 45 connecting the hinge portions 43 and 44.

Figure 8:
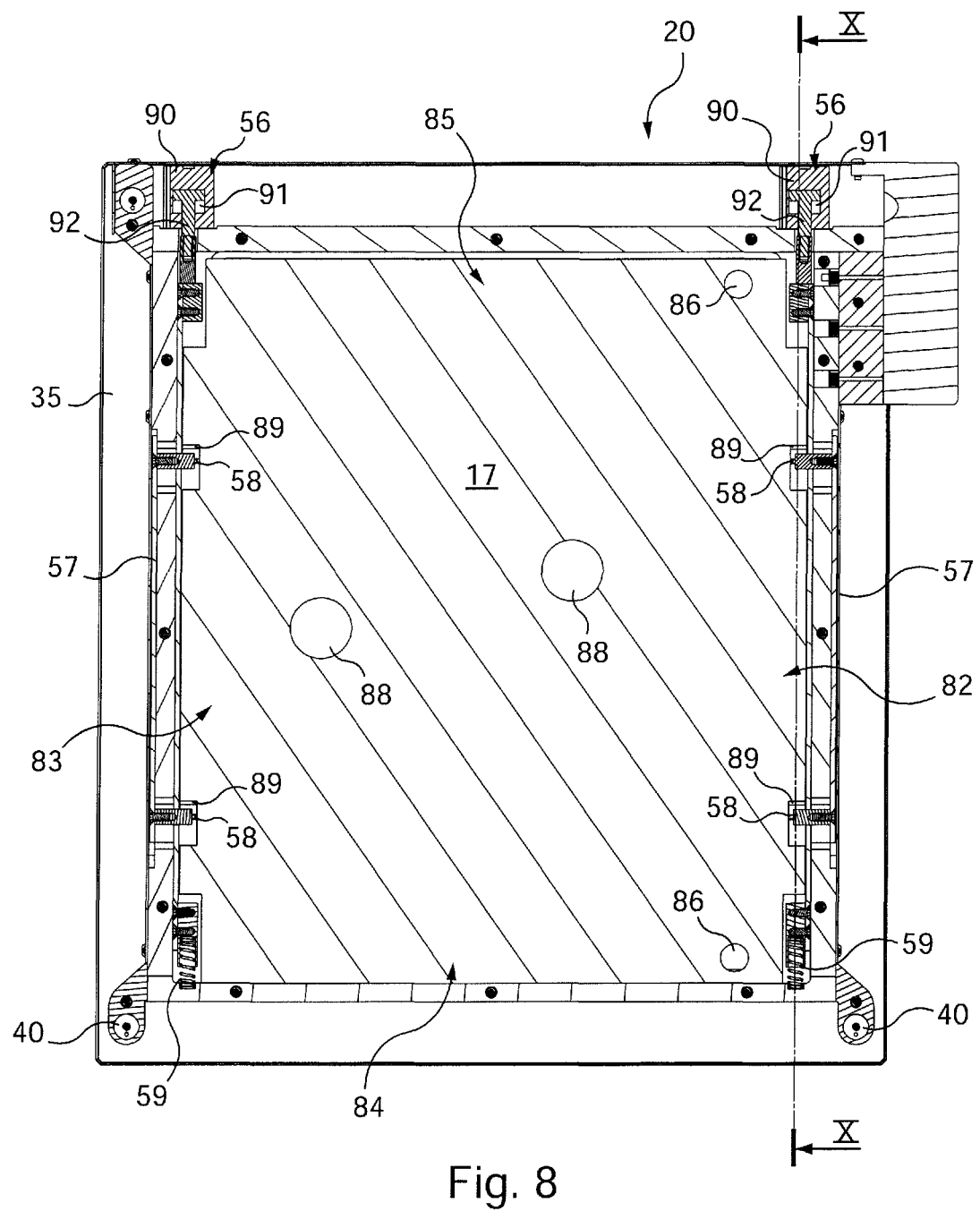
Figure 9:
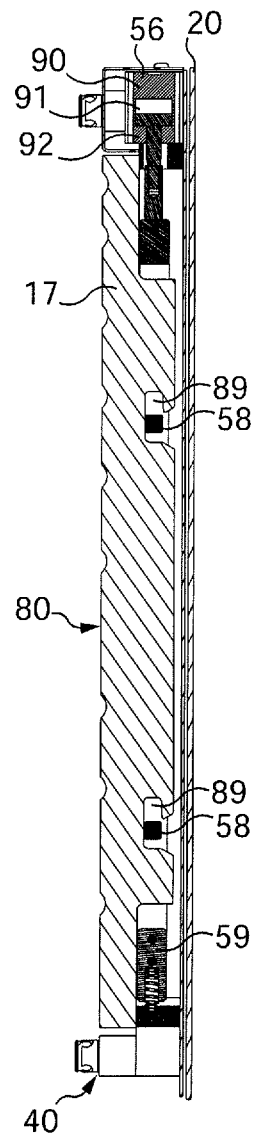
FIGS. 9 and 10 are cross-section views respectively on IX-IX and X-X of FIGS. 7 and 8 respectively.

The jacks 56 are illustrated in extended position in FIG. 7 and in retracted position in FIG. 8.

Each piston rod 92 is fastened to a rod 57, which rod 57 is also fastened to a spring 59.

The pneumatic chamber 91, when it is under pressure, biases the piston 92 against the spring 59. When the piston 92 is at end of travel the spring 59 is in retraced position (FIGS. 7 and 9) and the piston 92 is in extended position.

The rods 57 have thus been moved translationally downward, the shell 17 has been inserted against the sides 36 and 37 of the frame 35 of the door 20, with its reference surface 80 turned outwardly, and the locking bolts 58 of each rod 57 have been inserted into the corresponding recesses of the shell 17.

When the pneumatic chamber 91 of each jack 56 is at atmospheric pressure, spring 59 urges piston 92 via rod 57 towards the other end of travel position of that piston 92. When that position has been reached, spring 59 is in extended position, and the piston in retraced position.

The rods 57 have thus been moved translationally upward with their locking bolts 58 each having entered into a lock strike 89 of the shell 17 in order to lock that shell 17 in the door 20.

The shell 16 has a flat reference surface 95 and shaping channels 96 recessed relative to the reference surface 95, each facing a corresponding shaping channel 81.

Generally, the surfaces 80 and 95 have similar dimensions and the arrangement of the shaping channels 96 is the mirror image of the set of the shaping channels 81.

The shaping channels 81 and 96 are of semi-elliptical cross-section.

The surfaces 80 and 95 may be applied against each other with the channels 81 and 96 in register with each other to delimit a network of cavities which are each generally tubular.

The shell 16 has a first side 145 and a second side 146 that is an opposite side to the first side 145, a third side 147 and a fourth side 148 that is an opposite side to the third side 147, which third and fourth sides 147 and 148 each meet the first and second sides 145 and 146.

The shell 16 furthermore has, on the opposite lateral walls 98 and 99, dowels 100 adapted to be engaged, by virtue of a vertical translational movement from top to bottom when the shell 16 is against the chassis 25, in the hooking claws 26 disposed on that chassis 25.

Furthermore, on those same opposite lateral walls 98 and 99, the shell 16 has rods 101 for manipulating the shell 16, which rods 101 are longer than the dowels 100.

This manipulation is carried out by the user of the device 1, or with the help of a winch, which may for example be electric.

Thanks to the inclination and the weight of the shell 16, and thanks to the engagement of the dowels 100 in the hooking claws 26, the shell 16 is securely fastened to the chassis 25.

On its flat reference surface 95, the shell 16 furthermore has a re-entrant portion 102 which is extended downwardly by a slanting surface 103, the slant of which is directed inwardly of the device 1.

This slanting surface 103 enables the provision of access to the bay 6 comprising the containers.

Pipes (not shown) connected to the connectors 11 of the circuit 8, and in particular disposed at the location of the third side 147 of the shell 16, may also be connected to the containers.

Figure 14:
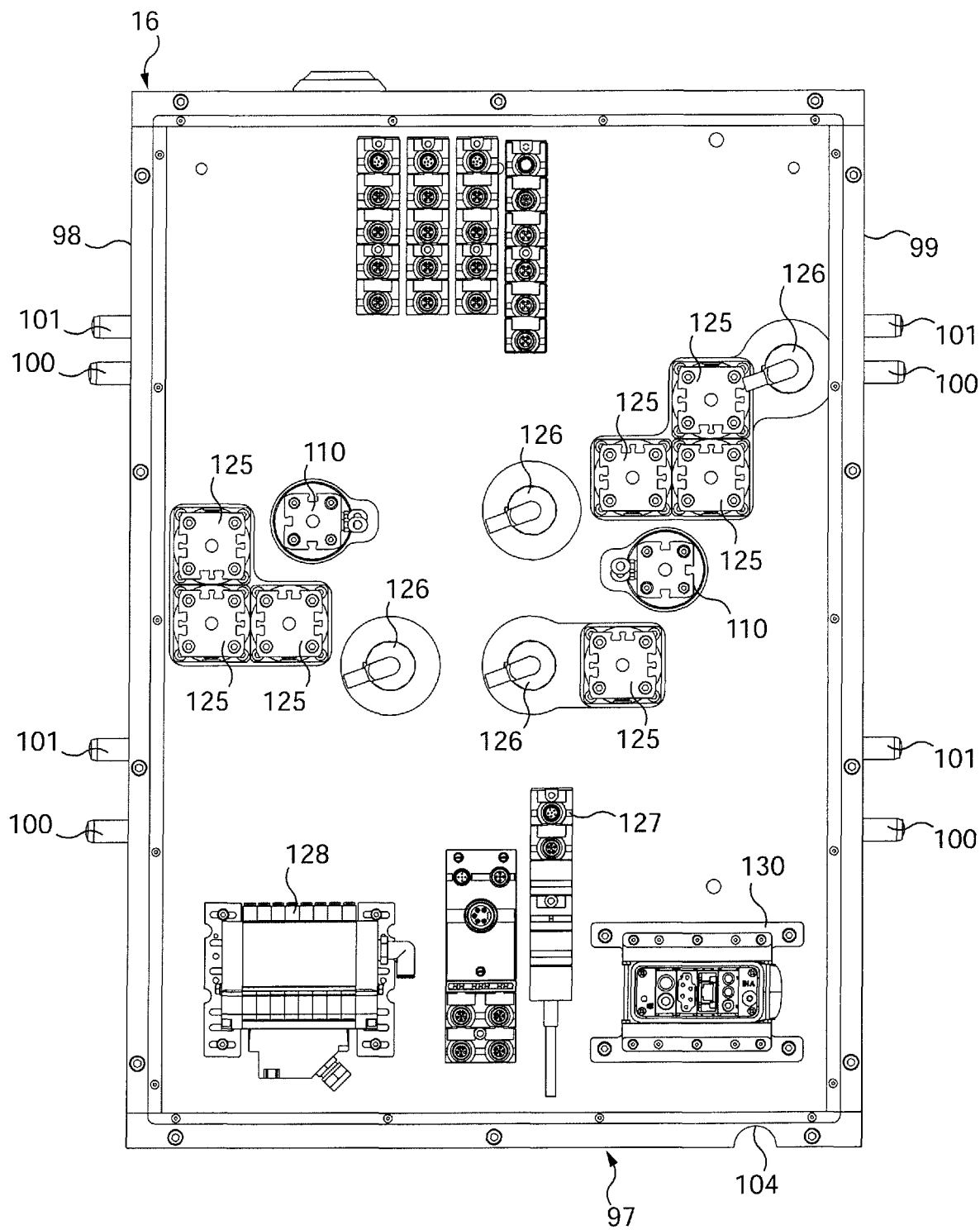
FIG. 14 is a view from behind of the first shell, with a back panel removed.

On a lower face 97, the shell 16 further comprises a channel 104 of inverted gutter shape emerging on the slanting surface 103 (FIGS. 1 and 14).

This channel 104 serves as a fool-proof device on installation of the shell 16 on the chassis 25 of the base 2, in order for the reference surface 95 to be turned inwardly.

The shell 16 further comprises, at the location of its fourth side 148, three hooking studs 106, of which two are disposed on respective opposite sides of the shell 16, the third being disposed substantially at the center of the fourth side 148 of the shell 16, with those three studs 106 being evenly spaced from each other.

As can be seen in FIG. 2, these studs 106 are adapted pass through the positioning apertures 73 of the bag 10 for the suspension of the latter on the shell 16.

Furthermore, the distal end of these same hooking studs 106 is adapted to be inserted into the positioning holes 86 of the shell 17 in the closed door position.

The shell 16 comprises two positioning dowels 107 for positioning the door 20, one of which is situated on the fourth side 148 of the shell 16 close to a hooking stud 106 situated at the top left of that shell 16, the other positioning dowel 107 being situated at the other extreme, that is to say at the bottom of the shell 16, between two shaping channels 96 at the location of the third side 147.

These positioning dowels 107 are adapted to pass through the apertures 77 of the bag 10, and the distal end of these positioning dowels 107 is adapted to be inserted into the positioning holes 87 of the shell 17.

The shell 16 further comprises two locking holes 108 which are situated at the locations where there are the most channels 96 serving for the formation of the conduits 13, since it is at these locations that the force of pressure is greatest during the treatment. The locking holes 108 are thus at least partially surrounded by channels 96.

These locking holes 108 are arranged so as to face the locking through-apertures 75 of the bag 10 when it is disposed on the shell 16, and also to face the corresponding locking holes 88 of the shell 17 in the closed door position.

The locking holes 108 of the shell 16 are passed through by the ball-lock pins 110, of which the details will be provided below, for the locking together of the shells 16 and 17 when the door 20 is in its closed position, and for the clamping of the bag 10 in the circuit 8.

As can be seen more particularly in FIGS. 11 to 13, each ball-lock pin 110 comprises a body 111, and an annular shoulder 112 provided with a transverse face 113 and connected to a head 114.

Four rods 115 project from the transverse face 113 to be inserted into apertures (not shown) formed in the body of the shell 16 in order to fasten the body 111 to the shell 16.

The body 111 comprises a pneumatic chamber 116 and a piston 117, the piston 117 being mechanically connected to a rod 118 with a conical tip.

That rod 118 extends within the head 114 of the pin 110.

Three balls 119 are arranged so as to be able to project from the head 114 by passing through the apertures formed in that head 114.

The pin 110 is similar to a double-acting type jack and this pin 110 comprises two pneumatic connectors 120.

The head 114 of each pin 110 passes through the corresponding locking hole 108 of the shell 16, head 114 also passes through the corresponding locking aperture 75 of the bag, and head 114 lastly emerges into a corresponding locking hole 88 of the shell 17 in the closed door position.

One of the connectors 120 of the pin 110 enables a first portion of the pneumatic chamber 116 to be pressurized, so as to act on the piston 117. When the piston 117 is at end of travel, the balls 119 are in extended position, that is to say that they project from the head 114 to extend into the locking hole 88 of the shell 17 (FIG. 13).

The locking holes 88 are configured such that, when the balls 119 are extended, the shells 16 and 17 are securely locked.

For this, the locking holes 88 comprise a first portion having a first diameter, which first portion is adapted to face the bag 10 when that bag is clamped between the shells 16 and 17, then a recess, and lastly a second portion having a second diameter greater than the first diameter.

Thus, in the extended position of the pin 110, the balls 119 of each pin 110 project into the second portion of the corresponding locking hole 88, the first portion of that locking hole 88 preventing the pin from disengaging by blocking the balls 119.

The other connector 120 enables a second portion of the pneumatic chamber 116 to be pressurized, this second portion being opposed to the first portion, to urge the piston 117 towards the other end of travel position. When that position is reached, the balls 119 are in retracted position, that is to say they go back into the head 114 (FIG. 12).

In addition to the shells 16 and 17, the circuit 8 comprises, here installed on the back of the shell 16, as illustrated in FIG. 14, instruments required for the treatment of the biological liquid.

For example, there are illustrated pinch valves 125 comprising actuators to pinch a conduit 13 so as to prevent or allow the passage of liquid in that conduit 13, and sensors 126 of a physico-chemical value, for example pressure.

Also illustrated are a pneumatic distributor 128 and means for verification and control to perform various treatments of that liquid, which means are formed for example by a verification and command unit 127.

In the example illustrated in FIG. 14, the actuators of the valves 125 each comprise for example a body fastened to the shell 16 and a moveable pinching finger having a retracted position when the valve 125 is in open position and an extended position when the valve 125 is in closed position (not shown).

In the extended position, the moveable finger projects into one of the channels 96 (not shown).

Each sensor 126 is fastened to the shell 16 in register with a channel 96, with the distal end of the sensor 126 emerging into that channel 96, without actually having to touch the fluid (not shown).

Such sensors are well known and comprise for example pressure sensors which measure the pressure via the outer surface of the bag 10.

The shell 16 further comprises, here installed behind that shell 16, a female connector 130 enabling power to be supplied to the valves 125, sensors 126, the distributor 128 and the verification and control unit 127, which are integrated into that shell 16.

The supply is thus electrical (for power and control) and pneumatic.

This female connector 130 is situated at the bottom right of the shell 16 (viewed from behind).

Figure 15:
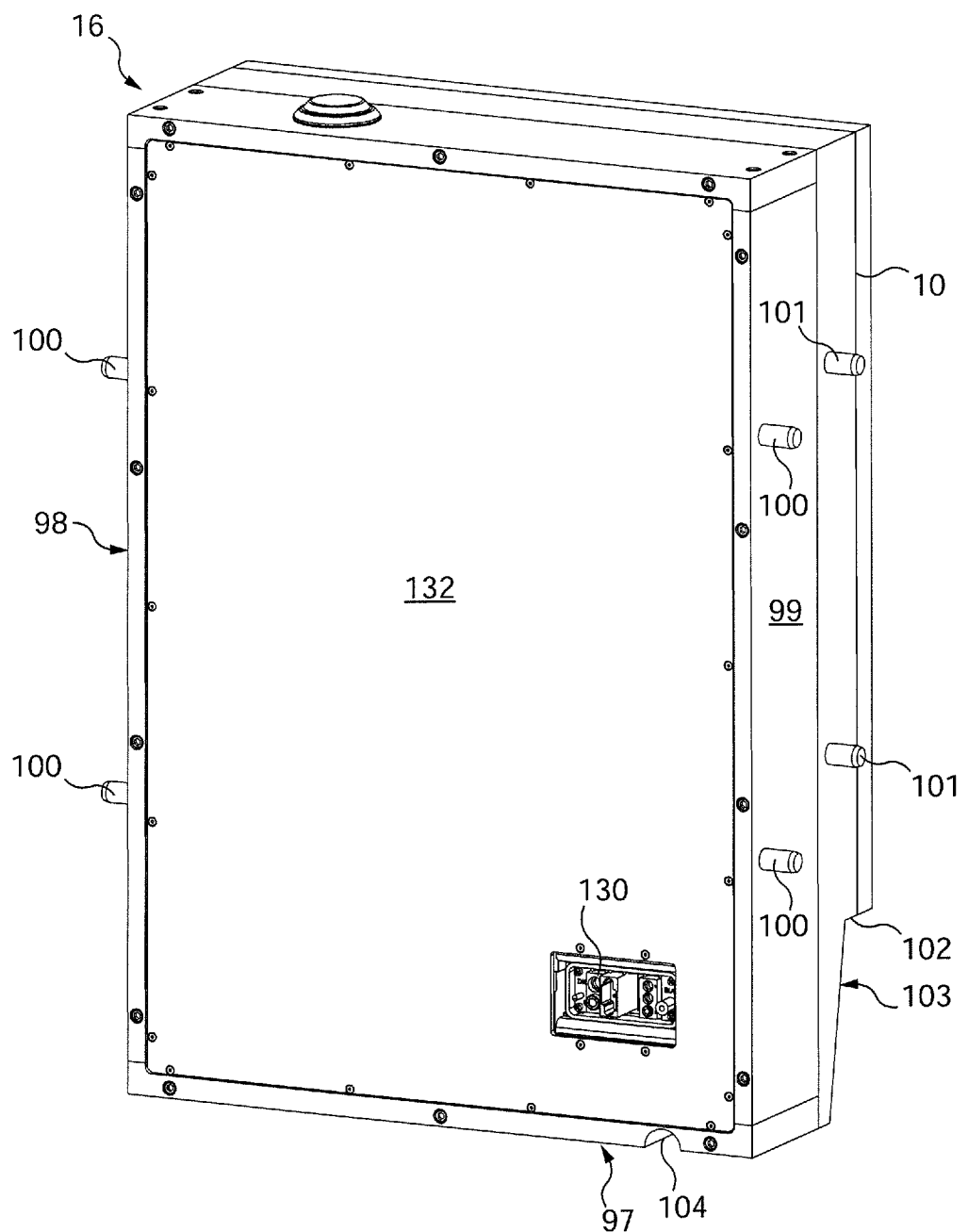
FIG. 15 is a similar view to FIG. 14, with the back panel.

As illustrated in FIG. 15, when the rear part of the shell 16 is covered by a back panel 132, only the access to the female connector 130 is possible.

A male connector 135 arranged on the base 2 of the device 1 can be connected to the female connector 130 of the circuit 8.

Figure 17:
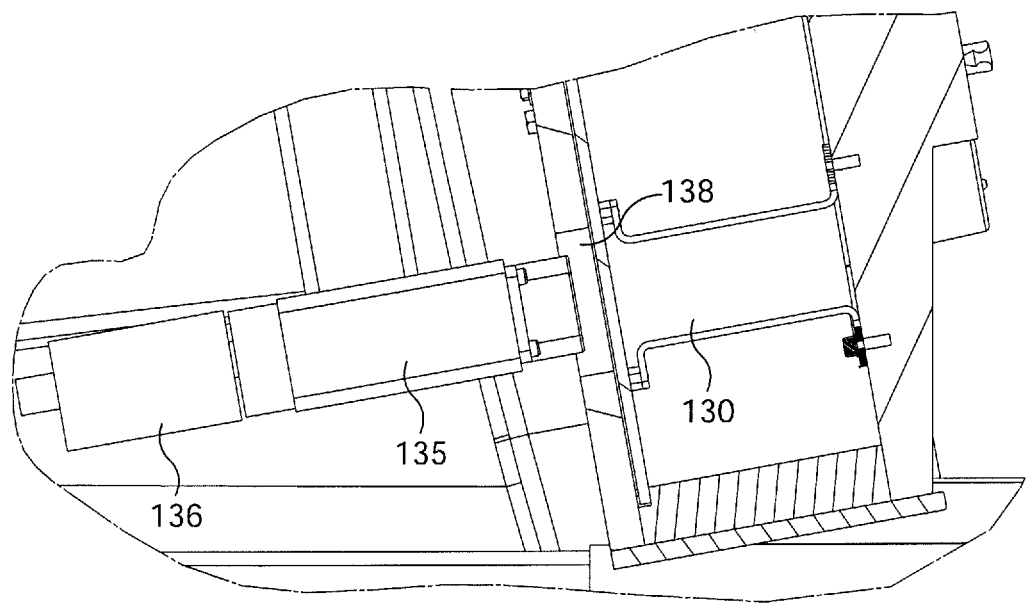
FIGS. 17 and 18 are partial cross-section views of the device, diagrammatically showing the male and female connectors respectively in a non-connected and connected state.
Figure 18:
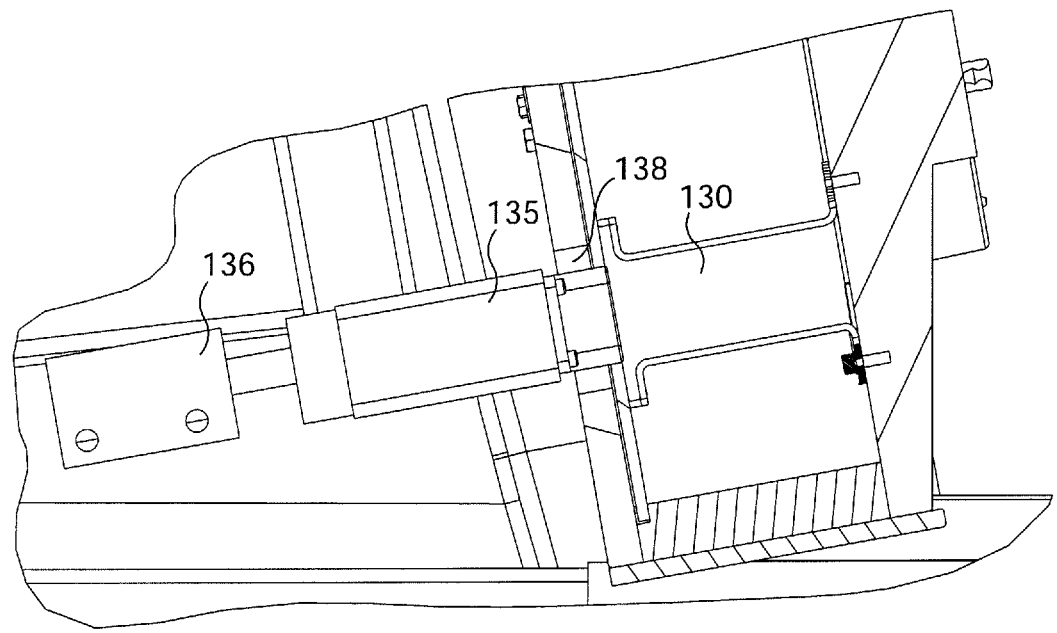

As is illustrated in FIGS. 16 and 17, the male connector 135 is moveable, by the action of a pneumatic jack 136 carrying the male connector 135 at its end, and this male connector 135 is adapted to pass through an opening 138 formed in the third side 142 of the chassis 25 for its connection to the female connector 130 (FIG. 18).

A description will now be made of the assembly of the circuit 8.

The shell 16 is fastened to the chassis 25 of the base 2, by virtue of the dowels 100 which locate in the hooking claws 26.

The male and female connectors 135 and 130 are connected together by virtue of the pneumatic jack 136 which makes that male connector 135 moveable, for the electrical and pneumatic supply of the circuit 8.

The bag 10 is next fastened by suspension onto the shell 16, by virtue of the positioning apertures 73 of that bag 10 which are passed through by the hooking studs 106 of the shell 16.

In the other position of the device in which the shell 17 is away from the shell 16, the shell 17 is assembled onto the frame 35 of the door 20 then locked by virtue of the system 55 of rods 57 of the door 20.

The door 20 is next closed so as to clamp the bag 10 between the shells 16 and 17. The device is thus in closed door position.

When the door 20 is closed, its positioning is provided in particular by virtue of the dowels 107 of the shell 16, by virtue of the positioning apertures 77 of the bag 10 and by virtue of the positioning holes 87 of the shell 17.

The door 20 is locked onto the front face 5 of the base 2 via the devices 29 and 40, respectively of the chassis 35 and of the door 20.

The shells 16 and 17 are next locked via the ball-lock pins 110 which furthermore enable the bag 10 to be clamped between the shells 16 and 17.

The connection of the surrounding treatment components (not shown) to the connectors 11 of the bag 10 is then carried out (if not already done before the mounting of the bag 10), via pipes, in particular flexible pipes.

These surrounding treatment components are formed in particular by one or more pumps, for example of the diaphragm type, and/or by a source container containing the product to treat and/or by a treated liquid collecting container and/or by a chromatography column.

These surrounding treatment components are disposed on one or more other devices, for example juxtaposed to the device 1.

These other devices are advantageously carts like the device 1.

These connections are greatly facilitated by virtue of the lateral clearances formed around the bag 10.

Of course, these connections may be formed before fastening the bag 10 by suspension onto the shell 16, without being hindered subsequently, that is to say at the time of suspending that bag 10 on the shell 16, by the hinge system.

Bag 10 is then inflated: the connectors 11 for liquid are obturated and a pneumatic agent is injected by the connector provided for that purpose (not shown).

The effect of the inflation of the bag 10 is that the films 65 and 66 respectively conform to the face of the shell 16 which presents the surface 95 and the channels 96, and the face of the shell 17 which presents the surface 80 and the channels 81.

The conduits 13 of elliptical section are formed at the location of the channels 81 and 96.

The press 9 and the bag 10 thus form a circuit 8 for treating biological liquid which is ready to be placed in service.

As the biological liquid is treated in the circuit formed by the press 9 and by the bag 10 which have to be protected from contamination, the bag 10 is provided with obturating plugs in place on each of the connectors 11 for liquid and on the connector for a pneumatic agent (not shown) and it is sterilized, for example by gamma irradiation. The pneumatic agent injected inside the bag 11 is purified.

For example, the pneumatic agent is compressed air purified by a hydrophobic filter, such as an AERVENT® available from the company Millipore, connected to the inflating connector (not shown).

Figure 19:
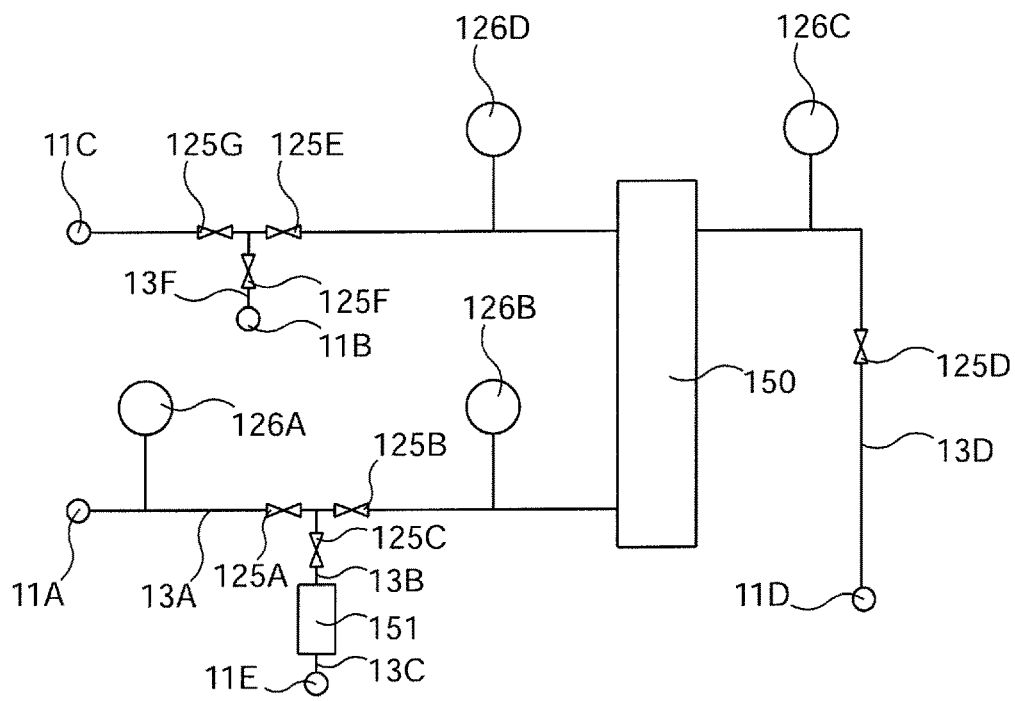
FIG. 19 is a diagrammatic view of the biological liquid treatment circuit of the installation.

FIG. 19 diagrammatically shows the circuit 8 provided by press 9 and bag 10. In this circuit the valves 125A to 125G are respectively formed by an actuator, and by the portion of the shell 17 against which the conduit 13 presses when it is pinched by the finger.

Connector 11B serves to inject the liquid to treat into a loop formed by conduit 13E, by the feed container connected to connector 11C, by the feed pump of which the inlet side is connected to another connector of the feed container and of which the delivery side is connected to the connector 11A, by the conduit 13A and by the filter.

On injection of the liquid to treat by connector 11B, all the valves are open, except for the valves 125E and 125A.

Once the product to treat has been transferred into the feed container, the valves 125F and 125C are closed, whereas the other valves are open and the feed pump is put into operation, such that the liquid to treat flows in the aforementioned loop.

On passage into the filter, the product to treat is purified with the retentate passing into the conduit 13E and the filtrate passing into the conduit 13D, then being evacuated to the drain.

When the liquid has sufficiently circulated in the loop and has attained the required characteristics of purity and concentration, its evacuation is performed to the collecting container connected to the connector 11E, by passing the valve 125B to the closed position and the valve 125C to the open position, the treated liquid thus attaining connector 11E by passing via filter 151 where the liquid undergoes a final filtration.

It should be noted that, in addition to the operations described above, the circuit is capable of implementing various other operations by virtue of the conveying network 12 formed by the conduits 13A to 13F and the valves 125A to 125G.

The sensors 126A to 126B are all pressure sensors here. They enable the proper operation of the installation to be verified, and in particular to detect any occurrence of excess pressure (sensor 126A) and to ensure proper operation of the filter (sensors 126B to 126D).

In a variant not illustrated, the hinge system comprises a door having a horizontal hinging axis rather than a single hinge situated in a corner. This door having a horizontal hinging axis is fastened to the top or bottom of the front face of the base of the device. Like the single hinge, this door having a horizontal hinging axis enables lateral clearances to be created over a major portion of the outline of the bag.

In a variant not illustrated, the door is removable, that is to say that it is independent from the base, and it is mounted on the base for its fastening thereto.

In a variant not illustrated, the jacks of the rod system are of double-acting type, or are electrical or hydraulic, rather than pneumatic.

In a variant not illustrated, the ball-lock pins are of single-acting type, or are electrical or hydraulic, rather than pneumatic.

In other variants not illustrated, other mechanisms may be used instead of the rod system, ball-lock pins and hooking claws.

In variants not illustrated, the inflation of the bag is carried out prior to the clamping of the bag, or partially before and partially after the clamping of the bag.

In still another variant not illustrated, there is no such prior inflation of the bag, since the conduits of the bag are directly formed by the conveying of the fluid into the bag, at the time of treatment.

In a variant not illustrated, rather than being dispersed over the same shell, the sensor or sensors of physico-chemical values are disposed on different shells; and/or no sensor is provided. The instrumentation is of course different depending on the treatment to carry out on the biological liquid.

In a variant not illustrated, the bag is triangular or circular rather than rectangular, and the case arising the shells are adapted to the shape of the bag, as well as, if desired, the door and the base. For example, in the case of a triangular bag, the door has only three sides and the hinge system is configured such that it forms lateral clearances at least at the location of the remaining two sides.

In other variants not represented:
- instead of being in one piece, the shells are formed by a set of modular members associated with each other to delimit the different portions of the circuit, which members are provided with marks or labels to ensure that they are correctly disposed relative to each other. The marks and the labels comprise for example reference numbers or codes and may be of the RFID type;
- the shells are of a material other than polyoxymethylene, for example stainless steel, or aluminum, or of another plastics material in particular having a high density, or of ceramic or wood;
- the shell 16 only comprises two hooking studs 106, or more than three, and, the case arising, the bag 10 comprises respectively only two or more than three positioning apertures 73, and for the shell 17 only comprises two or more than three positioning holes 86, those studs, apertures and holes being evenly spaced, or not;
- the shell 16 comprises more than two positioning dowels 107 and the case arising, the bag 10 comprises more than two positioning apertures 77, and the shell 17 comprises more than two positioning holes 87, those studs, apertures and holes being evenly spaced, or not;
- the shell 16 comprises more than two locking holes 108 and the case arising, the bag 10 comprises more than two locking apertures 75, and the shell 17 comprises more than two locking holes 88;
  - the films of the bags are of a material other than the PureFlex™ film, for example of another film with several layers compatible with biological liquids such as the film HyQ® CX5-14 available from the company Hyclone industries, or the film Platinum UltraPac available from the company Lonza;
- the physico-chemical value measured by the sensors 126 is temperature and/or pH and/or conductivity in combination or as an alternative to pressure;
- the shaping channels are of circular section rather than semi-elliptical cross-section;
- the pump or pumps of the other devices are of peristaltic type rather than diaphragm type; and
- the device is not in the form of a cart but is placed on another support, for example on a table, and/or
- all the surrounding treatment components are disposed with the device on the same cart, or on the same support, which is different from a cart.

It should be noted more generally that the invention is not limited to the examples described and represented.

The invention claimed is:

1. A device for a biological liquid treatment installation, comprising:
   a base having a front face;
   a movable door movable between an open and a closed position, said movable door having a perimeter;
   a circuit comprising a plurality of connectors and a network having conduits for conveying liquid between said connectors, which circuit comprises a bag comprising two flexible films and said connectors, which circuit further comprises a press comprising a first shell disposed upright on said front face of said base and a second shell mountable on said first shell, said first shell and second shell cooperating with said bag to form, between said flexible films, by clamping of said bag between said first shell and said second shell, the conduits of said network;
   a hinge system hinging said door relative to said base, said hinge system being disposed only on one side of said door so as to form, in the closed door position, lateral clearance between the door and the base over the rest of the perimeter of the door, so as to enable free access to the connectors.

2. The device of claim 1, wherein the two said flexible films of said bag are joined to each other and delimit a zone for treatment of said liquid according to a closed outline, said connectors emerging on the inside and on the outside of at least one side of said outline.

3. The device of claim 1, wherein said bag further comprises first through apertures on one side of said bag for its positioning, and said first shell comprising studs for hooking said bag to an upper part of said first shell, said hooking studs passing through said first through apertures of said bag.

4. The device of claim 1, wherein said hinge system comprises a single hinge disposed at a corner of said door, and said single hinge comprises a first hinge portion fastened to said corner of said door and a second hinge portion fastened to a lateral face of said device, which lateral face is connected to said front face.

5. The device of claim 1, wherein said hinge system has a pivot axis about which said movable door pivots between said open and closed position, and wherein said pivot axis is offset from a joining plane formed between said first shell and second shell in the closed door position.

6. The device according to claim 1, further comprising a locking system configured such that it locks together said first shell and said second shell.

7. The device according to claim 6, wherein said locking system comprises at least one ball-lock pin provided with a body, a head and balls and having an unlocked state and a locked state, said ball-lock pin being fastened to said first shell, said head passing through said first shell and a second through aperture and emerging into a first hole of said second shell, said balls entering said head in said unlocked state of said ball-lock pin and projecting from said head in said locked state of said ball-lock pin.

8. The device according to claim 1, wherein when said door is in said closed door position, said second shell is disposed in said door, and when said door is not in said closed door position, said bag is carried only by the first shell.

* * * * *